United States Patent [19]
Zimmerman et al.

[11] Patent Number: 5,652,342
[45] Date of Patent: Jul. 29, 1997

[54] HETEROFUNCTIONAL CELLULAR IMMUNOLOGICAL REAGENTS, VACCINES CONTAINING SAME AND METHODS FOR THE USE OF SAME

[75] Inventors: Daniel H. Zimmerman; Donald A. Elliott, both of Bethesda, Md.

[73] Assignee: Cel-Sci Corporation, Alexandria, Va.

[21] Appl. No.: 354,751

[22] Filed: Dec. 8, 1994

Related U.S. Application Data

[63] Continuation of Ser. No. 985,750, Dec. 4, 1992, abandoned, which is a continuation of Ser. No. 731,394, Jul. 17, 1991, abandoned, which is a continuation of Ser. No. 206,381, Jun. 14, 1988, abandoned.

[51] Int. Cl.$^6$ .................. C07K 14/705; A61K 39/385
[52] U.S. Cl. .................. 530/403; 424/185.1; 424/193.1; 530/300; 530/350; 530/402
[58] Field of Search .................. 424/184.1, 185.1, 424/193.1; 514/2, 8; 530/395, 350, 402, 403; 435/69.3

[56] References Cited

U.S. PATENT DOCUMENTS

| | | | |
|---|---|---|---|
| 4,400,376 | 8/1983 | Sanderson | 424/88 |
| 4,478,823 | 10/1984 | Sanderson | 424/88 |
| 4,599,230 | 7/1986 | Milich et al. | 424/89 |
| 4,599,231 | 7/1986 | Milich et al. | 424/89 |
| 4,605,512 | 8/1986 | Schaller et al. | 260/112.005 |
| 4,681,760 | 7/1987 | Fathman | 424/85 |
| 4,683,136 | 7/1987 | Milich et al. | 424/89 |
| 4,818,527 | 4/1989 | Thornton et al. | 424/88 |
| 4,822,606 | 4/1989 | Snyderman et al. | 424/88 |
| 4,835,255 | 5/1989 | Weissman et al. | 530/350 |

FOREIGN PATENT DOCUMENTS

| | | | |
|---|---|---|---|
| 0177023 | 4/1986 | European Pat. Off. | 530/402 |
| 8606413 | 11/1986 | WIPO | C12Q 1/68 |
| 8800057 | 1/1988 | WIPO | A61K 39/00 |

OTHER PUBLICATIONS

Jolivet, M.E. et al, Infect. Immun., 55:1498–1502 (1987).
Leo, O. et al, J. Immunol., 139:3556–3563 (1987).
Francis, M.J, et al, Nature, 330:168–170 (1987).
Good, M.F. et al, Science, 235:1059–1062 (1987).
Beachey, E.H. et al, Exp. Med., 166:647–656 (1987).
Ozaki, S. et al, J. Immunol., 138:4133–4142 (1987).
Milich, D.R. et al, Proc. Natl. Acad. Sci. USA. 85:1610–1614 (1988).
Science 235(4791):865–70, 1987. J.G. Guillet, et al. "Immunological self, non–self discrimination."
Nature 324:260–262, 1986. J.G. Guillet, et al. "Interaction of peptide antigens and class II major histocompatib. complex antigens."
J. Immunol. 133(4):2067–74. R. Shimonkevitz, et al. "Antigen recognition by H–2 restricted T cells . . . " Oct. 1984.
J. Immunol. 136(7):2498–2503. 1986. I. Berkower, et al. "Molecular mapping of a Histocompatibility–restricted . . . "
Synthetic Peptides as Antigens, John Wiley & Sons, New York, J.H. Humpfrey "Regulation of in vivo immune responses: few principles and much ignorance."

Byers, et al. in Basic & Clinical Immunology (1980). pp. 296–305. "Tumor Immunology".
Carbone, et al. in Fundamental Immunology (1989) pp. 541–544, "MHC Control of T Cell Recognition."
Weiss, in Fundamental Immunology (1989) pp. 359–369, "T Lymphocyte Activation".
Maloy, Immunol. Res., 6:11 (1987).
Margulies et al, Immunol. Res., 6:101 (1987).
McCluskey et al, J. Immunol., 136:1472 (1986).
Germain et al, Ann. Rev. Immunol., 4:281 (1986).
Bluestone, Immunol. Res., 6:67 (1987).
McCluskey et al, J. Immunol., 137:3881 (1986).
Ozato et al, J. Immunol., 137:3881 (1986).
Fremont et al, Science, 257:919 (1992).
Swain, Proc. Nat. Acad. Sci., 78:7101 (1982).
Goldstein et al, J. Immunol., 140:3707 (1988).
Potter et al, J. Exptl. Med., 166:956 (1987).
Ghann et al. J. Virol., 61:2639 (1987).
Nencioni et al, J. Immunol., 139:800 (1987).
Liu et al, Science., 239:395 (1988).
Burt et al, Eur. J. Immunol., 17:437 (1987).
Burt et al, Molec. Immunol., 24:379 (1987).
Chrétien et al, J. Immunol., 141:3129 (1988).
Palker et al, Proc. Nat. Acad. Sci., 85:1932 (1988).
Connolly et al, J. Exptl. Med., 168:325 (1988).
Potter et al, Nature, 337:73 (1989).
Connelly et al, Proc. Nat. Acad. Sci., 87:2137 (1990).
Salter et al, Nature, 345:41 (1990).
Nissen et al, J. Immunol., 139:1022 (1987).
Parham et al, J. Biol. Chem., 258:6179 (1983).
Van den Elsen et al, J. Immunol. Meth., 112:15 (1988).
Streicher et al, Proc. Nat. Acad. Sci., 81:6831 (1983).
Parham et al, Nature, 325:625 (1987).
Clayberger et al, Nature, 330:763 (1987).
Claman, J. Amer. Med. Assoc., 258:2834 (1987).
Good et al, Science, 235:1059 (1987).
Pierschbacher et al, Cell, 26:259 (1981).
Mazerolles et al, Cell, 56:497 (1988).
D'Souza et al, Science, 242:91 (1988).
Loftus et al, Science, 249:915 (1990).
Ferguson et al, Proc. Nat. Acad. Sci., 88:8072 (1990).
Cammarota et al, Nature, 356:799 (1992).
Fourth Edition of the "Sequences of Proteins of Immunological Interest" edited by E. A. Kabat et al (1987) and published by the U.S. Dept. of Health and Human Services pp. 337–348.
Sherman et al, Science, 258:815 (1992).
Matsumura et al, Science, 257:927 (1992).

Primary Examiner—Thomas M. Cunningham
Attorney, Agent, or Firm—Sherman and Shalloway

[57] ABSTRACT

The present invention relates to a heterofunctional cellular immunological reagent comprising at least two T cell specific binding ligands covalently linked together, wherein one of the T cell specific binding ligands binds to a specific class or subclass of T cells and another of the T cell specific binding ligands is an antigen associated with disease or a causative agent of disease, or epitope thereof. The present invention also relates to vaccines containing the heterofunctional cellular immunological reagents and methods for the use of the same.

5 Claims, No Drawings

HETEROFUNCTIONAL CELLULAR IMMUNOLOGICAL REAGENTS, VACCINES CONTAINING SAME AND METHODS FOR THE USE OF SAME

This is a Continuation of application Ser. No. 07/985,750, filed on Dec. 4, 1992 (now abandoned); which in turn is a Continuation of U.S. application Ser. No. 07/731,394, filed Jul. 17, 1991, now abandoned; which in turn is a Continuation of U.S. application Ser. No. 07/206,381, filed Jun. 14, 1988, now abandoned.

FIELD OF THE INVENTION

The present invention relates to a heterofunctional cellular immunological reagent comprising at least two T cell specific binding ligands covalently linked together, wherein one of the T cell specific binding ligands binds to a specific class or subclass of T cells and another of the T cell specific binding ligands is an antigen associated with disease or a causative agent of disease, or epitope thereof. The present invention also relates to vaccines containing the heterofunctional cellular immunological reagents and methods for the use of the same.

BACKGROUND OF THE INVENTION

In cell mediated immunity, a disease causing agent, such as a virus, is engulfed by a specialized cell called the antigen presenting cell (hereinafter "APC"). The APC breaks up the virus and fragments the antigenic determinants of the virus, i.e., viral specific polypeptides, into polypeptide fragments. These fragmented antigenic determinants are then transported to the cell surface of the APC. At this time, the APC also produces or modifies the major histocompatability complex molecules Class I and Class II (hereinafter "MHC Class I" or "MHC Class II", respectively), which are heavily involved in cell mediated immunity and which are produced within and transported to the surface of the APC. MHC Class I molecules specifically bind to cytotoxic/suppressor T cells (Tc/s) and MHC Class II molecules specifically bind to helper/accessory T cells (Th). The MHC molecules contain at least two binding sites, i.e., an antigen binding site known as agretope binding site, which is highly variable between MHC molecules for different agretopes, and a site which binds to the T cell, i.e., the T cell specific binding ligand, which is highly conserved (see Bjorkman, P. J. et al, *Nature*, 329: 506 (1987) and Bjorkman, P. J. et al, *Nature*, 329: 512 (1987)).

T cells are activated by the combination of (1) the binding of the fragmented antigenic determinants, present on the surface of the APC, to the surface of the T cells and (2) the binding of the highly conserved region of the MHC molecules, present on the surface of the APC, to the surface of the T cells. Usually, binding by the fragmented antigenic determinants or the highly conserved region of the MHC molecules alone to the surface of the T cells does not give rise to activation of the T cells since to do so would give rise to an unregulated and indiscriminate polyclonal activation of most, if not all, T cells and could result in pathogenic conditions. The binding of the MHC molecules to the surface of the T cells is in part mediated through the agretope, i.e., the binding of the antigen to the MHC molecules acts as a signal to the MHC molecules to bind to the surface of the T cells (see Bjorkman, P. J., *Nature*, 229: 506 (1987)). In addition, the MHC molecule contains recognition sites so that unless the APC and the T cell contain the same MHC molecules with the same genetic composition, they are recognized as "not-self" and the desired interaction cannot successfully occur. The resulting activated T cells can then recognize the disease causing or associated agent, e.g., virus infected cell, tumor cell, etc., in the bloodstream or elsewhere, as foreign and acts to kill such. This gives rise to cell mediated immunity to the disease caused by, e.g., the virus, without any antibody, or humoral immunity, involvement.

The APC, typically a macrophage, also produces and releases Interleukin 1 (hereinafter "IL-1") as a consequence of the interaction and processing of the antigen. IL-1 interacts with the T cell as a part of the activation process of the T cell. IL-1 causes activated T cells to produce Interleukin-2 (hereinafter "IL-2"). However, as with most hormones, IL-1 activity is generalized, i.e., it is not specific to a particular antigen but, rather, is involved in invoking a generalized inflammatory response.

Since MHC molecules are very large and highly polymorphic, antigenicity problems arise when administering such to a subject. Further, there is a high variability of agretopes and MHC molecules. Thus, it is difficult to isolate an appropriate MHC molecule for a disease causing or associated agent of interest so as to be able to form a complex thereof which can thereby activate T cells specific to a disease of interest.

In an embodiment of the present invention, the above-discussed problem is overcome by employing only a portion of the MHC molecules which bind to T cells, i.e., the highly conserved region thereof, and covalently linking such to an antigen associated with disease or causative agent of disease, or epitope thereof of interest, thereby forming a heterofunctional cellular immunological reagent and avoiding the necessity of isolating suitable or using large and polymorphic, MHC molecules. Further, in some cases, one of the reasons for a failure to respond to an antigen is a lack of antigen processing and/or appropriate MHC molecules. The heterofunctional cellular immunological reagent of the present invention overcomes this problem.

The clinical and industrial immunologists working in AIDS have not focused on the correlation of cell mediated immunity and disease since most of their assays are based on humoral immunity mechanisms. Cell mediated immunity, because of its slow reactions, the requirement for a living cell derived from an intact host and the MHC restriction inherent in the system have deflected attention away from cell mediated immunity. Cell mediated immunity has remained, therefore, somewhat of a "black box" with inputs and outputs defined but little understood in the way of internal mechanisms.

The rapidity of the re-activation of AIDS or herpes viruses indicates that re-activation cannot be a result of the breakdown of humoral response mechanisms. That is, re-activation occurs in a short number of days while serum antibodies are still abundant. In part because of the above circumstantial evidence in humoral response and in part because of other evidence in cellular mechanisms, a breakdown of cell mediated response mechanisms is implicated in re-activation of these disease causing agents.

In the case of tuberculosis (hereinafter "TB"), another disease where cellular immunity is paramount, IL-2, also known as T cell growth factor, can restore the in vitro cellular immune response to the mycobacterium. Since IL-1 is available in subjects afflicted with TB, a defect in the stimulation of IL-2 production by the cells implies a failure of the APC presentation or recognition process.

Exogenously provided IL-2 can restore, at least in part, in an in vitro assay system with AIDS patients, cell mediated immunity activity to Human Immunodeficiency Virus (hereinafter "HIV"). This suggests that with AIDS there is also a deficiency in IL-2 production, even though IL-1 production is above normal. AIDS infected patients also have either poor or ineffective antibody dependent cellular cytotoxicity (hereinafter "ADCC"), antibody complement cytotoxicity (hereinafter "ACC") or natural killer (hereinafter "NK") activity, even at early stages before any clinical signs of AIDS related complex (hereinafter "ARC") or AIDS.

In an embodiment of the present invention, a vaccine for diseases, such as AIDS, is provided which specifically stimulates cellular immunity to diseases, such as AIDS.

There are currently a series of in vitro assays for cell mediated immunity which use cells from the host both as the substrate cell that initiates or stimulates the reaction for which the assay has been developed and as the target to assess cell mediated immunity. These in vitro assays include the cytotoxic T lymphocyte assay (hereinafter "CTL"); lymphoproliferative assays, e.g., tritiated thymidine incorporation; the protein kinase assays, the ion transport assay and the lymphocyte migration inhibition function assay (hereinafter "LIF") (Hickling, J. K. et al, *J. Virol.*, 61: 3463 (1987); Hengel, H. et al, *J. Immunol.*, 139: 4196 (1987); Thorley-Lawson, D. A. et al, *Proc. Natl. Acad. Sci. USA*, 84: 5384 (1987); Kadival, G. J. et al, *J. Immunol.*, 139: 2447 (1987); Samuelson, L. E. et el, *J. Immunol.*, 139: 2708 (1987); Cason, J. et al, *J. Immunol. Meth.*, 102: 109 (1987); and Tsein, R. J. et al, *Nature*, 293: 68 (1982)). These assays are disadvantageous in that they may lack true specificity for cell mediated immunity activity, they require antigen processing and presentation by an APC of the same MHC type, they are slow (sometimes lasting several days), and some are subjective and/or require the use of radioisotopes.

In an embodiment of the present invention, a diagnostic assay for cell mediated immunity is provided which overcomes the above-described problem.

SUMMARY OF THE INVENTION

An object of the present invention is to provide a heterofunctional cellular immunological reagent which specifically interacts with the cellular immune system.

Another object of the present invention is to provide a vaccine for the prevention or treatment of disease by stimulating cellular immunity to the disease using the heterofunctional cellular immunological reagent.

Still another object of the present invention is to provide a method of prevention or treatment of disease by stimulating cellular immunity to the disease using the heterofunctional cellular immunological reagent.

A further object of the present invention is to provide a method of diagnosis of disease by assaying for the presence of T cells, which are active against the disease, using the heterofunctional cellular immunological reagent.

In one embodiment of the present invention, the above-described objects have been met by a heterofunctional cellular immunological reagent comprising at least two T cell specific binding ligands covalently linked together, wherein one of the T cell specific binding ligands binds to a specific class or subclass of T cells and another of the T cell specific binding ligands is an antigen associated with disease or a causative agent of disease, or epitope thereof.

In a second embodiment, the above-described objects of the present invention have been met by a vaccine for the prevention or treatment of disease comprising, as an active ingredient, a pharmaceutically effective amount of a heterofunctional cellular immunological reagent and a pharmaceutically acceptable carrier or diluent.

In a third embodiment, the above-described objects of the present invention have been met by a method of prevention of disease comprising administering the vaccine to a disease susceptible subject.

In a fourth embodiment, the above-described objects of the present invention have been met by a method of treatment of disease comprising administering the vaccine to a subject afflicted with the disease.

In a fifth embodiment, the above-described objects of the present invention have been met by a method of diagnosing disease comprising assaying for the presence of T cells in a subject, which are active against the disease, using the heterofunctional cellular immunological reagent.

DETAILED DESCRIPTION OF THE INVENTION

As discussed above, in one embodiment of the present invention, the above-described objects have been met by a heterofunctional cellular immunological reagent comprising at least two T cell specific binding ligands covalently linked together, wherein one of the T cell specific binding ligands binds to a specific class or subclass of T cells and another of the T cell specific binding ligands is an antigen associated with disease or a causative agent of disease, or epitope thereof.

As used herein, the expression "T cell specific binding ligand" refers to the entire molecule which binds to the surface of the T cell or only the T cell binding portion of the molecule, preferably only the T cell binding portion of the molecule.

The particular type of T cell to which the T cell specific binding ligands bind is not critical to the present invention. Examples of such T cells include helper T cells, accessory T cells, suppressor T cells and cytotoxic T cells. These T cells include subclasses thereof, for example, subclasses of helper T cells include those helper T cells necessary for antibody synthesis and those necessary for cytotoxic activity.

The particular T cell specific binding ligand which binds to a specific class or subclass of T cells employed is not critical to the present invention. The particular T cell specific binding ligand which binds to a specific class or subclass of T cells can be selected so as to bind to all mature T cells, only mature cytotoxic T cells, helper T cells, suppressor T cells or a specific class or subclass thereof. Examples of such T cell specific binding ligands include a T cell specific binding ligand which is also located on or binds to an APC, such as portions of MHC Classes I and II; portions of the Fc region of the heavy chain of immunoglobulins; $Ia^+$ molecules; lymphocyte function associated molecule-3 (hereinafter "LFA-3"); antibodies to CD-2, CD-3, CD-4 and CD-8; lectins such as concanvalin A, pokeweed mitogen, peanut agglutinin and phytohemagglutinin; lymphokines, such as IL-1 and IL-2; and other molecules such as d-poly-$(E/K)_n$ (60:40).

A small protein of MHC Class I, i.e., b-2-microglobulin (hereinafter "b-2-M"), which is found in various body fluids, such as serum, ascites and urine, has recently been shown to have biological properties indicating that such is a T cell specific binding ligand (see Nissen, M. H. et al, *J. Immunol.*, 139: 1022 (1987)). That is, the addition of this molecule to an in vitro $Cr^{+++}$ release cytotoxic assay system has an enhancing effect on CTL activity in both heterologous and homologous-systems, i.e., both human (heterologous) and murine (homologous) b-2-M give rise to the same biological effect in this assay system that uses murine cells. The sequence of b-2-M is reported in Gussow, D. et al, *J. Immunol.*, 139: 3132 (1987). The following sequences at positions 24–58 and positions 58–80, respectively, of b-2-M are believed to be particularly useful T cell specific binding ligands:

CYVSGFHPSDIEVDLLKNGERIEKVEHSDLSFSK (MW=4474)

KDWSFYLLYYTEFTPTEKDEYAC (MW=3396)

These two polypeptides are chosen to end at cysteines for several reasons. First, they represent a site that is probably outside of a linear epitope region. This is because in mature b-2-M, they are involved in the formation of intramolecular disulfide bonds. Second, they are chosen to take advantage of the cysteine to serve as a covalent linking site to the antigen associated with disease or a causative agent of disease, or epitope thereof.

A common sequence for CD-2 and LFA-3 has recently been reported (see Peterson, A. et al, *Nature*, 329: 842 (1987); and Seed, B., *Nature*, 329: 840 (1987)). CD-2, which is found on T cells, and a similar, if not identically derived molecule, LFA-3, which is found on macrophages, erythrocytes and nerve cells, are both implicated in various T cell receptor, ligand and modulation interactions. In particular, LFA-3 at positions 87–101:

KVSIYPTKGKNVLEK (MW=1956)

or the derivatives thereof where a cysteine (c) and two glycines (gg) are added:

cggKVSIYPTKGKNVLEK (MW=2228.3)

KVSIYPTKGKNVLEKggc (MW=2228.3)

or at positions 42–58:

KTSAKKKIAQFRKEK (MW=2043)

or the derivatives thereof:

KTSAKKKIAQFRKEKggc (MW=2314)

ccgKTSAKKKIAQFRKEK (MW=2314)

are believed to be useful T cell specific binding ligands.

Based upon the charged nature of these polypeptides, in addition to their possible direct use as a T cell specific binding ligand, a corresponding acidic polypeptide from within another region of LFA-3 is believed to be useful as a T cell specific binding ligand (see Breitmeyer, J. B., *Nature*, 329: 760 (1987)). That is, the carboxyl ultimate or penultimate sequence of LFA-3:

SRHRYALIPIPLAVITTCIVLYMNGIL (MW=3520)

or the derivatives thereof wherein an internal cysteine is replaced by amino-butyric acid (Abu) and/or an internal methionine is replaced by nor-leucine (Nle):

SRHRYALIPIPLAVITTAbuIVLYMNGIL (MW=3502)

SRHRYALIPIPLAVITTAbuIVLYNleNGIL (MW=3474)

or the derivative thereof:

cggSRHRYALIPIPLAVITTAbuIVLYNleNGIL (MW=3746)

As discussed above, these derivatives contain amino-butyric acid (Abu) and nor-leucine (Nle). The reason for the former substitution is to avoid the possibility of forming homofunctional conjugates by removing a source of sulfhydryl. The reason for the latter substitution is to remove a labile methionine which can cleave the peptide bond and form a homocysteine terminated polypeptide.

Antibodies to CD-2, CD-3, CD-4 and CD-8 are well known in the art (see Kung, P. et al, *Proc. Natl. Acad. Sci. USA*, 77: 4914 (1980)).

In cases where the sequence of the T cell specific binding ligands are not known, such as for antibodies to CD-2, CD-3, CD-4, CD-8, lectins and Ia+ the sequence must be determined in whole or part. It is possible to determine a theoretical sequence by determining the nucleotide sequence of the anti-sense nucleotide sequence and reading in reverse direction along the double stranded DNA backbone and preparing an anti-sense polypeptide (see Smith, L. R., *J. Immunol.*, 138: 7 (1987)) or by using the computer technology disclosed in U.S. Pat. No. 4,704,692.

Lectins, such as concanvalin A, are well known to be multivalent and to possess specific binding sites for their ligands (see Edelmann, G. M. et el, *Proc. Natl. Acad. Sci. USA*, 69: 2580 (1972)). In addition, it is well known that they cause a specific general activation of T cells and alter the pathway of events (see Zimmerman, D. H. et al, *J. Immunol.*, 111: 1326 (1973)). One such T cell specific binding sequence derived from concanvalin A is at position 80–110:

LNDVLPEWVRVGLDSASTGLYKETNTILSWS (MW=4040)

(see Wang, J. L. et al, *J. Biol. Chem.*, 250: 1490 (1975) and Edelmann, G. M. et al, *Proc. Natl. Acad. Sci. USA*, 69: 2580 (1972)).

It is well known that IL-1 has activity on several types of T cells, i.e., helper T cells and suppressor T cells, and is produced by the APC. Nencioni, L. et al, *J. Immunol.*, 139: 800 (1987) have described the following T cell specific binding sequence for IL-1 at positions 163–171:

VQGEESNDK (MW=1149)

or the derivative thereof:

VQGEESNDKggc (MW=1420)

Similarly, IL-2, produced by one type of T cell, i.e., T helper cells, interacts with receptors on the same and other T cells, i.e., Th and Tc/s cells (see Altman, A. et al, *Proc. Natl. Acad. Sci. USA*, 81: 2176 (1984)). IL-2 is reported to have an effect on immune antibody responses. IL-2 is believed by the present inventors to be useful as a T cell specific binding ligand, particularly at positions 34–39:

LEHLLL (MW=827)

and the derivative thereof:

cggLEHLL (MW=1098)

since these polypeptides compete with IL-2 is a binding bioassay (see Reiher, W. E. et al, *Proc. Natl. Aced. Sci. USA*, 83: 9188 (1987)).

Especially, IL-2 at positions 18–32:

TNSAPTSSSTKKTQL (MW=1802)

The amino acids "TSS-T" appears to be highly conserved from a variety of sources (see Kohtz, D. S. et al, *J. Virol.*, 62: 659 (1988)). Thus, the following derivatives of the above sequence found in retroviral protein sequences, which contains the TSS-T structure, may be employed as a T cell specific binding ligand:

TNSAPTSSSTKKTILggc (MW=2071)

AbuggTNSAPTSSSTKKTQL (MW=2055)

Liu, F.-T. et al, *Biochem,* 18: 690 (1979) describe an inhibitory/suppressive haptenic carrier for induction of antibody production that is a polymer of D-glutamic acid and lysine, referred to as poly-(D-GL) (60:40) or, using the present nomenclature for amino acids, referred to as d-poly-$(E/K)_n$ (60:40). In light of current knowledge of T cell receptors, it is believed by the present inventors that this polymer of D-glutamic acid and lysine encompasses a T cell binding ligand for the suppressor T cell and thus is believed to be useful in the present invention.

It is well known that both MHC Class I and II molecules are composed of multiple chains that are involved in multiple binding to each other, other membrane associated entities, antigens, agretopes, epitopes, and T cell receptors. One such molecule, b-2-M discussed above (Gussow, D. et al, *J. Immunol.,* 139: 3132 (1987)), is a small protein associated with MHC Class I. The above-mentioned sequences of b-2-M can be used for preparing trivalent heterofunctional cellular immunological reagents of the present invention. Similarly, sequences of LFA-3 or Ia+ are useful for preparing trivalent heterofunctional cellular immunological reagents of the present invention when one wants to involve both APC and T cells, in conjunction with the amino terminal polypeptide of b-2-M at positions 1–21:

INRTPKINVRSRHPAENGKSN (MW 2749)

or the derivatives thereof:

cggINRTPKINVRSRHPAENGKSN (MW3020)

INRTPKINVRSRHPAENGKSNggc (MW3020)

Since immunogenic for an antibody response, the following polypeptides of human chorionic somatotropin (hereinafter "HcS") at positions 166–174 may serve as a control to discriminate between those effects that are solely dependent upon the antigen epitope and those that also need the contribution of the ligand functional binding to a T cell which these HcS polypeptides do not (see Antioni, G. et al, *Mol. Immunol.,* 22: 1337 (1985)):

FRKDMDKVE (MW=1321)

and the derivatives thereof:

FRKDNleDKVE (MW=1293)

FRKDNleDKVEggc (MW=1565)

AbuggFRKDNleDKVE (MW=1547)

The T cell specific binding ligand or the T cell binding portion thereof or control polypeptide is commercially available or customized synthesized (Applied Biosystems (Foster City, Calif.), Biosearch (San Rafel, Calif.) Cambridge Research Biochemicals (Cambridge U.K.), Bachem Inc. (Torrance, Calif.), Serva (Westbury, N.Y.) or obtained from an appropriate natural source.

The T cell specific binding ligand is stored as a dry powder in a dessicated environment at −20° to −70° C.

In the following examples, all media and solutions are made up in freshly prepared glass distilled water or water of at least the same or greater quality unless otherwise indicated. These examples are provided for illustrative purposes only and are in no way intended to limit the scope of the present invention.

SYNTHESIS EXAMPLE 1

Isolation of the b-2-M T Cell Specific Ligand

The following example describes isolating and determining the T cell specific binding portion of a protein, i.e., b-2-M, whose amino acid sequence and nucleotide sequence are known. The approach described herein is also useful for a wide variety of other T cell specific binding ligands, e.g., lectins such as concanvalin A, pokeweed mitogen, peanut agglutinin and phytohemagglutinin; antibodies including those for cell surface proteins, such as CD-2, CD-3, CD-4, CD-8, etc.; as well as surface proteins such as LFA-3 and Ia+, where all of the sequences may not be known.

In this example, b-2-M extracted from cultured human B cells is purified by, e.g., affinity chromatography as described in Lerch, P. G. et al, *Mol. Immunol.,* 23: 131 (1986).

More specifically, the murine monoclonal antibody (anti-human b-2-M) producing hybridoma BBM.1 (ATCC No. HB-28) is grown in RPMI 1640 media containing 5.0 to 10% (v/v) fetal bovine serum. When 100 ml of cells at a concentration of $5\times10^5$ cells/ml are obtained, the cells are collected by centrifugation at 500×g at 15° to 25° C. for 5 min and resuspended in 50 ml of 0.01M potassium phosphate buffer (pH 7.0) containing 0.15M NaCl (hereinafter "PBS"), centrifuged as described above and resuspended in 50 ml of the same buffer.

Each of 15–25 (10–14 week old) Balb/c female mice, which have been inoculated 5.0 to 30 days, preferably 10 to 15 days, before with 0.5 ml of pristane (Serva, Westbury, N.Y.), is injected intraperitoneally with 0.1 to 1.0 ml of the resulting BBM.1 cells ($0.2\times10^6$ to $1\times10^6$ cells/ml), preferably 0.5 ml ($0.3\times10^6$ cells/ml). The inoculated mice are observed every other day for the next 10 days and starting on day 10, the mice are examined and ascites fluid collected by the "tapping", i.e., penetration, of the abdominal cavity, not more than every other day, with a 16–18 gauge needle (B bevel) and allowing the ascites fluid to drain into a sterile 15 ml centrifuge tube. After storage overnight at 4° C. to allow the fluid to clot, the clot is removed by centrifuging the sample at 1500×g at 2° to 8° C. for 15 min and the clear straw to reddish colored ascites fluid is collected. The collected fluid is pooled into 50 ml centrifuge tubes and stored at −20° to −70° C. until all of the mice that are being so tapped expire. All of the thus collected fluid from one group of mice, inoculated at the same time with the same lot of cells, is thawed, pooled, centrifuged as described above and aliquoted into 5.0 ml samples and frozen until used. Approximately 50 to 150 ml of fluid is collected depending upon the properties of the particular hybridoma employed, such as cell viability, growth rate and rate of production; the number of mice; and the overall efficiency of inoculation, collection and harvesting of fluid from the clotted material.

The antibodies are purified from the fluid (serum, ascites, tissue culture fluid) by precipitation and separation of the antibodies from many of the other fluid proteins. For example, the antibodies can be selectively precipitated by ammonium sulfate as follows.

The thawed fluid volume is recorded and the fluid is gently stirred while cooling to 4° C. in an ice bath. If serum is used, an equal volume of cold distilled or deionized water is slowly added. Then, while continually stirring, solid crystalline enzyme grade ammonium sulfate (Life Technologies, Inc., Gaithersburg, Md.) is added to an amount calculated as follows (total in g=volume in ml×0.706 g/ml×0.4). The mixture is then stirred for at least 1.0 hours and centrifuged at 3000×g at 2° to 8° C. for 45 min to separate the precipitated protein from the soluble material. Next, the precipitated protein is resuspended in a minimal volume, typically about 1.0 to 10% of the starting sample, using, e.g., PBS, and dialyzed against the same buffer at 4° C. for a minimum of 2 hours per buffer change and a minimum of 3 buffer changes, wherein the volume ratio of buffer to sample is at least 50:1. Then, the sample is clarified by centrifugation at 3000×g at 2° to 8° C. for 15 min and/or by ultrafiltration (0.2 μm filter size) before use or storage. If stored for any significant time, the sample is again clarified before use. If a fatty-like pellicle exists floating on top of the fluid phase, it can interfere with some of the subsequent steps and should be removed and discarded by either collection using a syringe and needle below the pellicle or by passage over a glass wool fiber filter pad.

More specifically, if 100 ml of ascites or serum is used, 100 ml of water is added along with 56.48 g of ammonium sulfate. The precipitated antibodies are resuspended in 5.0 ml of PBS and another 5.0 ml of PBS is used to wash the material into the dialysis bag. After dialysis against 1.0 liter of 0.01M potassium phosphate buffer (pH 7.0) for 18 to 72 hours and using at least 3 buffer changes of at least 1.0 liter each, the volume is about 15 ml. (Note, different buffers are employed for dialysis depending on the particular needs, i.e., ion exchange chromatography with a DE-52 (Whatman, Clifton, N.J.) column usually employs 0.001 to 0.05M potassium phosphate buffer (pH 6.5 to 7.5), preferably 0.01M potassium phosphate buffer (pH 7.0); or fast pressure liquid chromatography (hereinafter "FPLC") usually employs 0.01M Tris-HCl buffer (pH 7.5 to 8.5), preferably 0.02M Tris-HCl buffer (pH 8.0)).

The resulting material is applied to a DE-52 column (2.5×10 cm), eluted with, e.g., 0.01M potassium phosphate buffer (pH 7.0) and 2.0 ml fractions collected. The bulk of the antibodies are collected in fractions 5 to 15 for a total volume of 20 ml with an average protein content of >5.0 mg/ml (based on an $A_{280}$ of 1.5 for 1.0 mg/ml).

Alternatively, polyethylene glycol (PEG-6000) (Sigma Chemical Co., St. Louis, Mo.) can be used to precipitate antibodies from sera, ascites and is most useful with large volumes of dilute protein solutions, such as tissue culture fluid.

More specifically, the volume is recorded and the material cooled to 4° C. While gently stirring, fine granular PEG-6000 is added to bring the final concentration to the desired % (w/v). For IgM, the final concentration of PEG-6000 is about 5.0% (w/v). For IgG, the final concentration of PEG-6000 is about 12% (w/v), although in some cases up to 20% (w/v) may be required. The material is left to stir for at least 1.0 hour at 2° to 8° C. after all of the PEG-6000 is dissolved. Then, the material is centrifuged at ≧1500×g at 2° to 8° C. for 30 min and the precipitated and soluble material are separated by decanting. Next, the precipitate is dissolved in a minimal volume (1.0% (v/v) of sample volume) of PBS, dialyzed and fractionated as described above.

In another alternative, caprylic (octanoic acid) treatment can be carried out to purify antibodies from clotted sera, plasma ascites or tissue culture fluid.

More specifically, concentrated acetic acid is slowly added in small amounts thereto at 4° C. with gentle stirring so as to adjust the pH to 4 to 5. Then, caprylic acid (octanoic acid) is added slowly with stirring in an amount of, e.g., 3.3 ml per 100 ml of ascites or serum, for at least 1.0 hour at 2° to 8° C. and the material is centrifuged at 3000×g at 2° to 8° C. for 30 min to separate precipitated non-immunoglobulins and soluble antibodies. The precipitate is discarded, the pH of the supernatant is adjusted to 7.0 with 1.0M sodium phosphate buffer (pH 7.5), the supernatant is dialyzed against PBS, or 0.01M potassium phosphate buffer (pH 7.0), if DE-52 chromatography as described above is to be carried out.

To a solution of 0.1 to 20 mg/ml, preferably 10 mg/ml of antibody, purified as described above, is added an equal volume, preferably 5.0 ml, of freshly washed Affi-Gel-10 (BioRad, Richmond, Calif.) in 0.01M potassium phosphate buffer (pH 7.0). Then, the tube or container with the protein and gel is sealed and placed at 2° to 8° C. in a rotating capped vessel overnight in order to allow the coupling of the antibody to the gel matrix. The next day the liquid is decanted off and the gel is washed at least three times with a 10 fold volume of cold PBS. The settled gel is resuspended in an equal volume of 0.1M ethanolamine in PBS, stirred for 1 hour at 4° C., washed extensively with PBS and then "stripped" with an agent, such as a chaotropic buffer, e.g., 2.8M $MgCl_2$, which can be used to elute the T cell specific binding ligand, i.e., b-2-M, from the bound antibody. Next, the gel is re-equilibrated in PBS, and finally stored at 4° C. in PBS containing 0.01M EDTA and 0.1% (w/v) $NaN_3$. For initial use and after storage for long periods of time, i.e., greater than 1 week, the gel is first poured into a column (1.0 to 1.5×2.5 to 5 cm) which is washed with 50 ml each of PBS, 2.8M $MgCl_2$ and PBS.

Next, the T cell specific binding ligand b-2-M is prepared from cultured human B cells (HEL 92.1.7) (ATCC No. TIB-80). More specifically, HEL 92.1.7 cells are cultured in a suspension culture using RPMI 1640 containing 10% (v/v) fetal bovine serum. Approximately 1000 ml of cells, at a density of about 5×10$^5$ cells/ml are collected. The cells are then extracted for b-2-M as described by Lerch, P. G. et al, *Mol. Immunol.*, 23: 321 (1986).

Alternatively, the cells are suspended in 10 to 20 ml of cold 3.0M KCl and after allowing to sit for a brief time, the treated cells are centrifuged at 3000×g at 2° to 8° C. for 30 min so as to pellet and separate the solublized surface membrane released proteins from the insoluble material. To the solubilized membrane proteins is added a 1.0% (v/v) of Triton X-100. Then, the material is dialyzed against 3 changes of 1.0 liter each of cold PBS. After dialysis, the sample is clarified by centrifugation at 10,000×g for 30 min. The preparation may be filtered using a 0.2 μm filter if desired.

Thereafter, the sample is applied to the anti-b-2-M affinity column prepared as described above, eluted with 100 ml of PBS or more until the absorbance level in the eluent, as monitored by absorption at $A_{280}$, is less than 0.1% of the starting sample or is undetectable. Then, the T cell specific binding ligand, i.e., b-2-M is eluted with 2.8M $MgCl_2$, at a flow rate of 1 to 20 ml/hour. Individual fractions having a volume of 0.1 to 2.0 ml are collected depending upon the sample, buffer and column.

Size exclusion (molecular sieve) and/or desalting (buffer exchange) chromatography with appropriate sizing characteristics for the T cell specific binding ligand and buffer is carried out on the peak protein containing fractions from the affinity column described above to reduce the salt content from the 2.8M $MgCl_2$ and to separate aggregated material from native material. Neutral, non-dissociating buffers, e.g., PBS, or other saline buffers with pH ranges of 6.0 to 9.6 such as, Tris-HCl, 0.05M sodium barbital, 0.05M sodium borate or 0.1M sodium bicarbonate can be employed for this chromatography. In some cases, dissociating buffers, e.g., 5.0M guanidine HCl, 8.0M urea, 0.1 to 2.0% (v/v) detergents, such as Triton X-100 can be employed for this chromatography, especially for removal of aggregates. Buffers which are volatile for ease in lyopholization such as, 0.1 to 1.0M ammonium formate or 0.1 to 1.0M ammonium acetate can also be employed. Nonvolatile buffers are preferably employed if lyopholization is not required. The sample volume is about 1.0% (v/v) or less of the bed volume, the void position is about 0.3 to 0.4 of the bed volume, the internal volume is about 1.0 to 1.2 of the bed volume and the optimal fraction size is about 1.0% of the column. Collection of fractions begins upon application of the sample. The flow rate is as specified by the manufacture, preferably using mid-point to lower values.

Enzyme digestion of the resulting purified T cell specific binding ligand is then carried out to determine the T cell specific binding portion thereof. More specifically, 2.0 mg/ml of the purified T cell specific binding ligand is dissolved in an appropriate enzyme digestion buffer, such as 0.1M ammonium acetate (pH 7.0), and to 1.0 ml thereof is added 50 μl of a proteolytic enzyme, such as trypsin, chymotrypsin, thermolysin, proteinase K, *Staphylococcus aureus* protease, Submaxilaris protease, subtilisin, or clostripian, to achieve a weight ratio of enzyme to substrate of 1:50. For example, 0.1 ml of purified b-2-M at 20 mg/ml in PBS is added to 0.9 ml of 0.1M ammonium acetate (pH 7.0). Then, 50 μl of a 2.0 mg enzyme solution in water is added. Incubation is carried out at about 37° C. for time intervals of about 10 to 120 min. At this point, the reaction in, e.g., a 13×100 glass test tube capped loosely with a marble, is terminated by immersion of the tube to a depth of 2.0 to 4.0 cm in a boiling water bath for 5 min. The terminated reaction sample is then lyophilized, or in some cases 100 μl thereof is added to 10 ml of PBS, and assayed directly. The latter is carried out at the initial stages when it is not necessary to separate the digested polypeptides, i.e., it is only necessary to determine an allowable reaction condition for limited proteolysis to yield digested polypeptides. In this case, 6 replicate sets of reactions for each enzyme are prepared and termination is carried out after 0, 10, 20, 30, 60 and 120 min of incubation. Trypsin digestion is also performed on native and citraconylated T cell specific binding ligands to distinguish between lysine and arginine sensitive sites. Note, citraconylated lysines are resistant to trypsin hydrolysis.

More specifically, multiple preparations are separately prepared as follows with each enzyme and time point. 0.1 ml of a purified b-2-M preparation containing 20 mg/ml protein in PBS is added to 0.1M of ammonium bicarbonate (pH 7.0) and then 0.05 ml of a 1.0 mg/ml enzyme solution of trypsin, or proteinase K, or chymotrypsin, or thermolysin, *Staphylococcus aureus* protease or clostripain or Submaxilaris protease or subtilisin is added. For each time series, 6 identical preparations, in 13×100 mm glass test tubes covered with a glass marble that fits over the tube top, are prepared and the reaction terminated by immersion of the tube to a depth of over 3.0 cm in a boiling water bath for 5 min after 0, 10, 20, 30, 60 and 120 min of incubation. As discussed above, if comparable reactions (for trypsin only) are carried out with or without citraconic anhydride treated b-2-M polypeptide, only the arginine sites are sensitive to cleavage since the lysine sites are protected.

In some cases, selective chemical hydrolysis using, for example, CNBr to cleave methionines is employed in formic acid. Other cleavage sites with other agents or conditions have been reported (see Fontana, A., in *Meth. in Enzymol.*, 25: 419 (1972); Ozols, J. et al, *J. Biol. Chem.*, 252: 5986 (1977); and Hunziker, P. E. et al, *Biochem. J.*, 187: 515 (1980)).

Amino and carboxyl terminal amino acids are determined using either appropriate proteases as recommended by the manufacturer (Pierce Chemicals, Rockford, Ill.) or by a system for automated sequential degradation, separation and analysis, i.e., a "polypeptide sequencer" (Applied Biosystems, Foster City, Calif.). Also, it is often the case that the polypeptide will be analyzed for total amino acid content after hydrolysis for 24, 48 and 72 hours in boiling 6.0N HCl or using other appropriate means as recommended by the manufacturer of an "amino acid analyzer" (Beckman, Palo Alto, Calif.; and Applied Biosystems, Foster City, Calif.).

To detect a reactive polypeptide derived from the purified T cell specific binding ligand, a standard competition inhibition immunoassay is performed wherein the test specimen, e.g., enzyme-digested sample, is incubated at several dilutions with the ligand binding species prior to the indicator being incubated with a labeled indicator. Normally, replicates are carried out at at least 3 different dilutions, usually over 3 ten fold log, i.e., 1/10, 1/100, and 1/1000. With very concentrated or high affinity T cell specific binding ligand, higher dilution levels are employed, such as 1/10,000, 1/100,000, up to 1,000,000 or even greater.

The labelled indicator in this case is b-2-M that is coupled with an appropriate molecule such as Biotin-N-hydroxysuccimide ester (Biotin-NHS) (Pierce Chemical, Rockford, Ill.). Other labelled indicators include radioisotopes, fluorescent dyes or common color developing enzymes, such as horseradish peroxidase, can be employed in place of Biotin. The competition can be carried out with a monoclonal antibody or other ligand binding species, such as a T cell membrane. In the former case, after the appropriate pre-incubation of the diluted enzymatic or chemically digested materials and the Biotin-b-2-M conjugate at the optimal dilution, which is determined previously for that particular lot, the mixture of materials is reacted with the T cell or immobilized monoclonal antibody. Typically with a 1.0 mg/ml solution of b-2-M and an indicator/protein ratio of 2.0 the dilution will be 1:10,000. Immobilized monoclonal antibody can be employed if properly selected to recognize the same ligand as the T cell membrane component, i.e., if it competes with the T cell for binding to the native ligand. The use of non-living material is preferable for a number of reasons, including less dependence on sensitive critical and sometimes unavailable living material, ease of use and control of conditions.

After incubating the mixture of the competing species and the immobilized material (cells or antibody coated microplates), for example, at 37° C. for 120 min for monoclonal antibody coated microplates, or at 2° to 8° C. for 30 min for T cells, the cells or microplates are washed extensively with PBS, and the presence of the bound labeled species detected, directly if possible or developed as required. If development is required, a conjugate of avidin and either horseradish peroxidase or fluorescein is used at a dilution of 1:250 to 1:5000 and incubated as described above for the Biotin-derivative, and washed and processed as required to detect its presence.

Once a enzyme system is identified that digests the T cell specific binding ligand but does not substantially alter its activity, it is verified that the reactive polypeptide is indeed a polypeptide by a variety of techniques, such as RP-HPLC, high voltage electrophoresis and ascending thin layer chromatography.

For RP-HPLC, a C-18 column (Vydac 15 to 20 μm 300 Å pore size 30×5 cm) can be used. In this case, a gradient of a mixture of aqueous triethylammonium phosphate ("TEAP") (pH 2.25) and 60 or 70% (v/v) acetonitrile with 0.1% (v/v) aqueous trifluoroacetic acid (hereinafter "TFA") in TEAP can be used as an elution buffer. A flow rate of 2.0 ml/min for an analytical column and 80 to 120 ml/min for a preparative column can be employed. Polypeptides are detected by monitoring absorbance at $A_{220}$ (see Hoeger, C. et al, Biotechniques, 2: 134 (1987)).

For high voltage electrophoresis, two-dimensional separations using a solid support, such as Whatman 3MM paper, is carried out. A total of 100 to 400 μg of enzyme digested material is loaded onto the support by multiple additions and drying of 5.0 to 10 μl samples of enzyme digested material onto a spot in the corner, inside 1.0 cm in each dimension, of 23×23 cm paper. High voltage electrophoresis is carried out using a buffer system of pyridine: acetic acid: water (25:1:225 (v/v/v)) at 2.0 kV and 35 to 60 mA for 80 min at 2° to 8° C. After removing and drying, the support is rotated 90 degrees and then equilibrated in the solvent described below for thin layer chromatography (TLC) and chromatographed in the same manner. After drying, polypeptides are detected by the use of 0.0215% (w/v) of a commercial Ninhydrin Spray or fluorescamine dye (Hoffmann-LaRoche, Nutley, N.J.) in acetone and UV light.

For ascending TLC, 3.0 μl of lyopholized enzyme digested material is dissolved in 10% (v/v) acetic acid at 2.0 mg/ml. Among the useful commercially available TLC plates are those available from E. Merck (Darnstadt, West Germany). The sample (3.0 μl) is applied to the plates which are placed above an atmosphere saturated with a solvent system of pyridine:n-butanol:acetic acid:water (50:75:15:60 (v/v/v/v)) at 4° C. After allowing to equilibrate for 2 hours, the plates are introduced into the solvent to a depth of about 1.0 cm and allowed to develop overnight. Usually the solvent front advances up about 18 cm. The plates are then removed and dried at room temperature. After drying, the polypeptides are detected as described above. The polypeptides so detected are then eluted from the plates with 0.07% (v/v) ammonium hydroxide, followed by competitive inhibition analysis (if an appropriate dilution is allowable with the buffers or else lyophilized first to concentrate such).

The separated polypeptide may be fixed onto the plates with 2.0% (v/v) glutaraldehyde for 15 min, "blocked" with a mixture of 2.0% (v/v) serum of the same species as the enzyme conjugated antibody to be used later and 2.0 to 10% (v/v) bovine serum albumin in 0.1M Tris (pH 8.0) containing 0.15M sodium chloride. Then, the fixed polypeptide is analyzed for reactivity by reaction with about 0.1 μg of, e.g., Biotin- or enzyme-, such as horseradish peroxidase or alkaline phosphatase, conjugated antibody by incubation therewith for 1 to 18 hours at 4° to 37° C., washed with the same buffer and then developed with a precipitating color as per standard Western blot immunological procedures (Biotech, Rockville, Md.).

Alternatively, if the labelled indicator that the polypeptide reacts with is an antibody, the unlabelled antibody is dissolved in freshly prepared 0.15M sodium carbonate buffer (pH 9.5) at a concentration generally of about 0.1 to 10 μg/ml, and then added in an amount of 100 to 200 μl/well of microtiter plates (Immunlon Dynatech, Alexandria, Va. or BD, Oxnard, Calif.). This coated antibody, while reactive with the parent molecule and derivatives thereof, is of a different specificity than that of the labelled antibody. Thus, it does not compete, interfere or stimulate the binding of the other antibody but, rather, only serves as a means of attachment for the ligand that the other monoclonal antibody binds. The plates are covered for 2 hours at room temperature, washed 3 to 5 times with 0.01 to 5.0% (v/v) bovine serum albumin (hereinafter "BSA") along with 0.1% (v/v) Tween-20, or other mild detergent such as, Triton X-100, in PBS at 4° C. If necessary, 0.01% (v/v) PVP and/or 5.0 to 20 mg/ml of sugar, such as dextrose or sucrose are added for stability in the last few washes, dried and stored in a dark moisture free environment 4° C. In addition, if necessary, the wells may be fixed with agents, such as 0.25 to 2.0% (v/v), preferably 0.25% (v/v) of glutaraldehyde prior to blocking with BSA.

An appropriately diluted sample of polypeptide (1:100 to 1,000,000) in PBS containing 0.1% detergent, e.g., Tween-20, is added along with diluted animal sera of the same type as that of the detection conjugate (enzyme:antibody) and incubated at 37° C. for 30 min to 24 hours. Then, the wells are washed 5 times with PBS and an appropriate dilution of the detection conjugate (1/1000 to 100,000) in the same buffer is added incubated and washed as described above. Next, substrate is added and detection is carried out as described above.

In addition, the amino acid composition of the final product is determined and then compared with the predicted amino acid composition. A deviation greater than 5 to 10% is investigated in order to verify that the product is what is expected, and that the deviation is due to the hydrolysis condition used to determine the enzyme digest.

The particular antigen or epitope thereof which is associated with disease is also not critical to the present invention. Examples of such antigens include allergens, such as cat dander antigens, dust mite fecal antigens and food allergens such as wheat glutenin; or self-derived antigens, such as epidermal growth factor (hereinafter "EGF"), which is a breast tumor cell specific marker or carcinoebryonic antigen (hereinafter "CEA") or prostate acid phosphotase (hereinafter "PAP"), which are associated with colorectal carcinoma and prostate tumors, respectively; cell surface antigens; or antigens associated with auto-immunity such as diabetes, Rheumatoid arthritis and thyroiditis.

In addition, the particular causative agent of disease to which the antigen or epitope thereof is associated, is also not critical to the present invention. Examples of causative agents of disease include prions; viruses, such as HIV, Herpes Simplex Virus (hereinafter "HSV"), Epstein Bar Virus (hereinafter "EBV"), cytomegalo virus (hereinafter "CMV"), human B lymphotropic virus (hereinafter "HBLV"), varicella zoster virus (hereinafter "VZV"), adenovirus and hepatitis B virus: bacteria, such as streptococcus, diptheria, mycobacterium and troponema; fungi, such as candida; protozoa, such as giardia; and parasites, such as plasmodium, ascaris and leishmania.

Furthermore, the particular disease to which prevention, treatment or diagnosis is desired is not critical to the present invention and can include any disease associated with the above-described antigens or epitopes thereof.

Recently, several polypeptides have been reported that are able to generate antibodies that react with a prion protein having the following sequences at positions 90–102, 15–40 and 220–223, respectively (see Barry, R. A. et al, *J. Immunol.*, 140: 1185 (1988)):

GQGGGTHNQWNKPGGC (MW=1960)

MWTDVGLCKKRPKPGGWNTGGSYRYPGGC (MW=3685)

CGGKESNAYYDGRRSSA (MW=2109)

Chapman, M. D. et al, *J. Immunol.*, 140: 812 (1988) describe, for the cat dander antigen, referred to as Fel d I, an antigenic sequence at positions 1–33:

GITPAVKRDVDLFLTGTPDEYVEQVAQYKAPDV (MW=4213)

or the derivative thereof:

GITPAVKRDVDLFLTGTPDEYVEQVAQYKAPDVc (MW=4331)

A sequence that is shared by the early region protein E1b of adenovirus type 12 and gliadin, a wheat glutenin protein, is believed to have important implications in coeliac disease (see Karagiannis, J. S. et al, *Lancet, I:* 884 (1987) and Kagnoff, M. F. et al, *J. Exp. Med.*, 160: 1544 (1984)). That is, in gliadin at positions 211–217:

FRPSQQN (MW=983)

and the derivative thereof:

FRPSQQNggC (MW=1255)

The above epitope shared in common between adenovirus and gliadin can be considered illustrative of an association of autoimmune, allergic and infectious conditions. Another epitope associated with autoimmune and infectious conditions is that of mycobacterium purified protein derivative (PPD). This epitope has implications in adjuvant induced arthritis in animals (see Lider, O. et al, *Proc. Natl. Acad. Sci. USA*, 84: 4577 (1987)).

Epitopes of myelin basic protein (MBP) and collagen (see Ellerman, K. E. et al, *Nature*, 331: 265 (1988); Lider, O. et al, *Science*, 239: 181 (1988); and Kakimoto, K. et al, *J. Immunol.*, 140: 78 (1988)) are illustrative of epitopes involved in autoimmune encephalomyelitis and arthritis, respectively. Thus, epitopes of these proteins can be determined and employed in the present invention.

Examples of antigens or epitopes thereof of HIV which are associated with humoral immunity and thus which can be employed in the present invention include the envelope proteins of HIV, such as gp120 and gp41.

HIV gp41 has the following antigenic sequence at positions 594–605 (see Banapour, B. et al, *J. Immunol.*, 239: 4027 (1987)):

G(I/M)WGCSGK(L/H)(I/L)C

Since genetic variants exist which have substitutions at certain non-critical positions, these non-critical positions have been indicated by a "/" along with the possible amino acids for these positions enclosed by a "()". Thus, for example, a derivative of the above antigenic sequences of HIV gp41 can be as follows:

GIWGAbuSGKLIC (MW=1389)

Some animal experiments demonstrate that the following adjacent region of HIV gp41 at positions 609–620:

CTTAVPWNASWS (MW=1700)

while immunogenic in animals, may not be as immunogenic in humans (see Gnann, J. W. et al, *J. Infect. Dis.*, 156: 261 (1987)). The failure to be immunogenic can be the result of one or more defects. One such defect can be a failure to recognize an agretope due to the lack of an appropriate receptor. Similarly, the corresponding T cell may not be present for the desirable T cell class, e.g., helper T cells which recognizes the epitope are desired but, only cytotoxic T cells that recognize the epitope are present. Thus, other polypeptides including both regions, such as shown below are believed to be useful for the synthesis of heterofunctional cellular immunological reagents of the present invention.

G(I/M)WGCSGK(L/H)(I/L)CTTAVPWNASWS or in one form:

LGLWGCSGKLICTTAVPWNASWS (MW=3118)

or the derivatives thereof:

cggLGLWGCSGKLICTTAVPNASWS (MW=3389)

LGLWGCSGKLICTTAVPWNASWSggc (MW=3389)

If the sensitive sites of the internal cysteines are substituted with amino-butyric acid (Abu) the epitope has the sequence shown below:

LGLWGAbuSGKLIAbuTTAVPNASWSggc (MW=3353)

Another HIV envelope protein is gp120. One of the epitopes thereof associated with humoral immunity includes the sequence at positions 108–119 (see Gnann, J. W. et al, *J. Infect. Dis.*, 156: 261 (1987)):

ILSLWDQSLKPC (MW=1690)

Chanh, T. C. et al, *EMBO J.*, 5: 3065 (1986); Chanh, T. C. et al, *Eur. J. Immunol.*, 16: 1465 (1986); Kennedy, R. C. et al, *J. Biol. Chem.*, 262: 5769 (1987); and Kennedy, R. C. et al, *Science*, 231: 1556 (1986)) describe the same epitope using their sequence position nomenclature at positions 503–532:

VAPTAKRVVQRKRAVGIGALFLGFLGAG (MW=3340)

or the derivative thereof:

VAPTAKRVVQRKRAVGIGALFLGFLGAGggc (MW=3611)

One of the first synthetic polypeptides shown to be immunogenic, in terms of antibody generation, for HIV was that for the gp41 protein at positions 735–752:

(R/D)RPEGIEEEGGERDRDR(S/G)C or one form thereof:

RRPEGIEEEGGERDRDRSC (MW=2570)

(see Kennedy, P. C. et al, Science, 231: 1556 (1986)) and is believed to therefore be a useful polypeptide sequence in whole or in part.

Another one of the HIV proteins, gag p17, at positions 92–109:

IDVKDTKEALEKIEEEQN (MW=2438)

or the derivatives thereof:

abuggIDVKDTKEALEKIEEEQN (MW=2691)

IDVKDTKEALEKIEEEQNggc (MW=2709)

due to its similarity to thymosin alpha, has been discussed as a candidate for immunization to generate humoral antibodies (see Sarin, P. et al, Science, 232: 1135 (1986)). The sequence relationship to thymosin alpha strongly suggests the need and relevance to cellular immunity since thymosin alpha is considered to be an immune system hormone or immunomodulator.

Other HIV gag polypeptides from both the p17 and p24 region described by Gnann, J. W. et al, J. Infect. Dis., 156: 261 (1987) are believed to be useful in the present invention. These derivatives are important since some animals can recognize and make antibodies to these epitopes and serum antibodies are neutralized in an in vitro assay using these epitopes (see Ho, D. D. et al, J. Virol., 61: 2024 (1987); and Satin, P. et al, Science, 232: 1135 (1986)).

As discussed above HSV EBV CMV, HBLV and VZV antigens are also believed to be useful in the present invention. For example, Zweig, M. et al, J. Virol., 51: 340 (1984) describe for HSV gC, the following antigenic sequence at positions 128–139:

DRRDPLARYGSR (MW=1659)

or the derivative thereof:

DRRDPLARYGSRggc (MW=1932)

Bosch, D. L. et al, J. Virol., 61: 3607 (1987); and Weijer, W. J. et al, J. Virol., 62: 501 (1988) describe for HSV gD, the antigenic sequence at positions 1–30, especially at positions 9–21 and in particular, the amino acids at positions 10, 16 and 20:

KRALADASLKMADPNRFRGKDLPVLDQLTD (MW=3888)

or the derivatives thereof:

KRALADASLKMADPNRFRGKDLPVLDQLTDc (MW=4009)

Kinchington, P. R. et al, J. Virol., 62: 802 (1988) describes for the major DNA binding protein of VZV, the antigenic sequence at the carboxyl terminus:

PIKHNGITMEMI (MW=1602)

or the derivatives thereof:

PIKHNGITNleENleIggc (MW=1817)

AbuggPIKHNGITNleENleI (MW=1799)

Oba, D. E. et al, J. Virol., 62: 1108 (1988) describe for EBV gp85, the antigenic sequence at positions 518 to 533:

CSLEREDRDAWHLPAYK (MW=2467)

The surface antigen protein of hepatitis B virus has the following antigenic region at positions 144–159 (see Pfaff, E. M. et al, EMBO J., 1: 869 (1982)):

LRGDLQVLAQKVARTL (MW=2079)

or the derivative thereof:

LRGDLQVLAQKVARTLggc (MW=2350)

or using the nomenclature of others at positions 139–158 (see Bhatnagar, P. K. et al, Proc. Natl. Acad. Sci. USA, 79: 4400 (1982)):

CTKPTDGNCTCIPIPSSWAF (MW=2573)

or the derivative thereof:

CTKPTDGNAbuTAbuIPIPSSWAF (MW=2537)

The preS-2 region of hepatitis B virus is also antigenic, particularly at positions 99–121 (see Jolivet, M. E. et al, Infect. & Immunol., 55: 1498 (1987), and Aubibert, F. M. et al, Infect. & Immunol., 45: 261 (1984):

DYQGMLPVCPLIPGSSTTSTGPC (MW=2731)

or the derivative thereof:

DYQGNleLPVAbuPLIPGSSTTSTGPC (MW=2685)

Bacterially important epitopes are described in Beachley, E. H. et al, J. Exp. Med., 166: 647 (1987), e.g., the streptococcal epitopes of the approximately first 10 amino terminal region of the M protein of three strains of streptococci and a polypeptide containing these three different amino terminal sequences:

TVTRGTISDPRVFPRGTVENPVATRSQTDTSEKc (MW=4301)

or a derivative thereof where the lysine, which contains a potential reactive group, is substituted by glycine, which, since it is adjacent to the added cysteine not found in other variants at this location, suggests that it is outside of the primary epitope:

TVTRRGTISDPRVFRRGTVENPVATRSQTDTSEGc (MW=4230)

Jolivet, M. E. et al, Infect. & Immunol., 55: 1498 (1987) describe the following antigenic sequence for diphtheria toxin at positions 186–201:

CAGNRVRRSVGSSLKC (MW=1945)

or the derivative thereof when the internal cysteine is replaced by amino-butyric acid and two alanines are added:

aaAbuAGNRVRRSVGSSLKC (MW 2123)

The circumsporozoite stage protein of plasmodium, including but not limited to such species as falciparum, knowlensi, etc. referred to as CSP-1, has an internal repetitive sequence depending upon the species (see Lise, L. D. et al, Infect. & Immunol., 55: 2658 (1987); Ballou, W. R. et al, Science, 228: 991 (1985); Jolivet, M. E. et al, Infect. & Immunol., 55: 1498 (1987); Patarroyo, M. E. et al, Nature, 328: 629 (1987); and Good, M. F. et al, Science, 235: 1059 (1987)). The following antigenic sequences of CSP-1 are believed to be useful epitopes in the present invention:

NANPNANPNANPNANPNAC or (NANP)₄C (MW=1994)

Y(QAQGDGANAGQP)₂C (MW=2925)

c(QAQGDGANAGQP)₂y (MW=3106)

Other sequences of the CSP-1 used for vaccines include the repetitive sequence:

[(NANP)₁₅(NVDP)]₂ (MW=15047)

as well as the following two sequences at positions 103–116 and 323–349, respectively:

EKLRKPKHKKLKQP (MW=1992)

NNEEPSDKHIEQYLKKIKNSISTEWSPC (MW=3849)

(see Good, M. F. et al, Science, 235: 1059 (1987)). The latter sequences have been used for generation of an immune response either directly or indirectly by "helper T cell epitopes". The last sequence was shown to be restricted by the I-A and or H-2 MHC genes of certain phenotypes.

The amino terminal polypeptide sequence of another plasmodium protein, i.e., the 35 kd protein, having the following sequence, has been used for humoral responses (see Patarroyo, M. E. et al, Nature, 328: 629 (1987)):

WGGPANKKNAG (MW=1237)

or the derivatives thereof:

abuggWGGPANKKNAG (MW=1622)

WGGPANKKNAGggc (MW=1641)

Other polypeptides from malaria proteins which can be employed include those described in Etlinger, H. M. et al, J. Immunol., 140: 626 (1988); Sadoff, J. C. et al, Science 240: 336 (1988); Richars, R. A. et al, Infect & Immunol., 56: 682 (1988); Richman, S. J. et al, Proc. Natl. Acad. Sci. USA, 85: 1667 (1988); Weiss, W. R. et al, Proc. Natl. Acad. Sci. USA, 85: 573 (1988); Good, M. F. et al, J. Immunol., 140: 1645 (1988); Brake, D. A. et al, J. Immunol., 140: 1989 (1988); and Good, M. F. et al, Proc. Natl. Acad. Sci. USA, 85: 1199 (1988).

Oba, D. E. et el, J. Virol., 62: 1108 (1988) also describe the control polypeptide from human C9, a complement series protein, at positions 399–413:

CLIDDVVSLIRGGTRK (MW=2015)

As another control, epitopic sequences for the foot and mouth disease virus (hereinafter "FMDV") can be used, particular VP-1 having the following sequence at positions 141–160 (see Bittle, J. L. et al, Nature, 298: 30 (1983)) to which cysteine is added at the amino acid:

cVPNLRGDLQVLAQKVARTLP (MW=2652.2)

This epitope is of a similar size and composition to the above-described polypeptides and can serve as a control sequence for either replacement of the antigen associated with disease or a causative agent of disease, or epitope thereof or the other T cell specific binding ligand. Because of the addition of cysteine to the amino terminal, it can be linked by several mechanisms that utilize sulfhydryl linkages.

Still another control sequence is the following sequence of cytochrome c, believed to be representative of a non-pathogenic or non-disease condition, at positions 81–104 (see Fox, B. S. et al, J. Immunol., 139: 1578 (1987)):

IFAGIKKANERAELIAYLKQATKC (MW=3094)

The antigen associated with disease or a causative agent of disease, or epitope thereof or control polypeptide is commercially available or customized synthesized (Applied Biosystems, Foster City, Calif.), Biosearch (San Rafel, Calif.) Cambridge Research Biochemicals (Cambridge, U.K.), Bachem Inc. (Torrance, Calif.), Serva (Westbury, N.Y.) or obtained from the native source.

The antigen associated with disease or a causative agent of disease, or epitope thereof is stored as a dry powder in a dessicated environment at −20° to −70° C.

The particular size of the heterofunctional cellular immunological reagent of the present invention is not critical thereto. Generally, the heterofunctional cellular immunological reagent is about 20 to 100 amino acids in length, preferably about 40 to 60 amino acids in length.

The heterofunctional cellular immunological reagent of the present invention can be prepared by the use of bifunctional linkers. Examples of bifunctional linkers which can be employed in the present invention to covalently link the T cell specific binding ligand and antigen associated with disease or a causative agent of disease, or epitope thereof include N-succinimidyl-3-(2-pyridyldthio)propinate (hereinafter "SPDP") (Pharmacia, Piscataway, N.J.), which activates and allows formation of a bridge between two sulfhydryl groups of cysteines or a bridge between a derivatized (propinated-thiolyated) primary amino group and a cysteine; m-maleimidobenzoyl-N-hydroxy-succimide ester (hereinafter "MBS") (Pierce Chemical, Rockford, Ill.), which activates an amino group and then couples by a sulfhydryl group to a cysteine sulfydryl so as to form a disulfide bond between the two polypeptides; and 1-ethyl-3-(3-dimethylaminopropyl)carbodiimide (hereinafter "EDC") (Pierce Chemical, Rockford, Ill.), which can cross-link two polypeptides by sequentially activating the carboxyl group of one polypeptide and then adding such to an amino group of another polypeptide. N-isocyano-ethylmorphlin, bis-diazotized-benzidine, benzoquone and glutaraldehyde, which are other reagents commonly employed to link polypeptides, can be employed in the present invention and are available from Pierce Chemical, Rockford, Ill.; Eastman Kodak Chemicals, Rochester, N.Y.; Serva, Westbury, N.Y.; Sigma Chemical Co., St. Louis, Mo.; and E. Merck, Darnstadt, West Germany (see Briand, J. S. et al, *J. Immunol. Meth.*, 78: 59 (1985); Kitagawa, T. et al, *J. Biochem.*, 79: 233 (1976); Liu, F. T. et al, *Biochem.*, 18: 690 (1979); Ternynck, T. et al, *Immunochem.*, 14: 767 (1977); and Drevin, H. et al, *J. Immunol. Meth.*, 77: 9 (1985)).

The heterofunctional cellular immunological reagent of the present invention can also be prepared by chemical synthesis or by using recombinant DNA techniques, i.e., where the nucleotide sequence of the T cell specific binding ligand and antigen associated with disease or causative agent of disease or epitope thereof are adjacent to each other and inserted into an appropriate expression vector so that a single molecule is synthesized recombinantly.

In order to prepare the heterofunctional cellular immunological reagent of the present invention, it is first necessary to analyze the sequences that are to be covalently linked so as to determine what amino acids can be substituted with a stable (or less reactive) amino acid, such as substitution of nor-leucine for methionine, or amino-butyric acid for a cysteine, in the chemical synthesis of the polypeptide. If one of the desired sequences contains a cysteine and a substitution with amino-butyric acid is not practical, this polypeptide can be linked using MBS or EDC. Substitution of the cysteine with amino-butyric acid is practical if it is not essential that the cysteine be linked by a disulfide bond to another cysteine or another reactive group. If a cysteine is at the amino or carboxyl terminal of the polypeptide it is less likely to be in the T cell specific ligand binding portion or an epitope. Therefore, conjugation at this site can be carried out using MBS or SPDP as a bifunctional linker group.

Depending upon the synthetic reactions or other conditions, protection of other reactive groups, such as the epsilon amino of lysine, or groups of arginine, histidine and the carboxyl or derivatives thereof of aspartic and glutamic, may not be necessary. In this case one can proceed directly to the linking of the T cell specific binding ligand and antigen associated with disease or a causative agent of disease, or epitope thereof so as to produce the heterofunctional cellular immunological reagent without prior derivatization for protection.

Protection, such as the temporary blockage of the epsilon amino of lysine is accomplished by pretreatment of the polypeptide with citraconic anhydride, maleic anhydride or other similar acid anhydrides that will reversibly displace the H on the amino groups. After the construction of the heterofunctional cellular immunological reagent, the acid group added to the amino when the H is displaced is in turn displaced by acid treatment.

SYNTHESIS EXAMPLE 2 USING SPDP

The following example describes the production of a heterofunctional cellular immunological reagent comprising an HIV epitope covalently linked using SPDP to the T cell specific binding ligand portion of b-2 -M.

3.4 mg (2.0 µmole) of the derivative of the HIV gp41 epitope:

AbuTTAVPWNASWS (MW=1682)

is dissolved in 1.0 ml of 0.1M sodium phosphate buffer (pH 7.5) at 15° to 25° C. in a conical stirring reaction vessel. To this solution is added 0.1 ml of a freshly prepared SPDP solution (20 µmole) (6.4 mg/ml of SPDP dissolved in ethanol or DMSO). (Note, if the water soluble forms of substituted SPDP are available they should be employed since this avoids the undesirable use of organic solvents such as DMSO or ethanol.) The reaction mixture is stirred for 0.5 hours at 15° to 25° C., after which time the material is chromatographed using a desalting column, such as Bio-gel P2, P4 P6 or P10 (BioRad, Richmond, Calif.) or the Sephadex equivalent. In this example, preferably P-2, P-4 or Sephadex G-10 (Pharmacia, Piscataway, N.J.) is used. The column's internal dimensions are 1.5×75 cm (although dimensions of 0.9 to 2.5×50 to 100 cm are also satisfactory).

Elution is carried out using 0.05M sodium phosphate buffer (pH 7.0) containing 0.15M NaCl, at a flow rate of 10 to 25 ml/hr. (If the material is to be lyopholized, an acceptable alternative buffer which can be used is 0.05 to 0.1M ammonium acetate buffer (pH 7.0).)

About 100 or so equal fractions (between 0.5 and 1.0 ml in size for the preferred column) are collected. Then, the column is eluted with at least 100 ml more of the same buffer. The elution profile is monitored by recording the absorbance at an appropriate wavelength, typically between $A_{210}$ and $A_{290}$. Under ideal conditions of gel size, flow rate, buffer, conformation of polypeptides, etc., there may be some resolution, especially on the leading edge, of substituted and non-substituted polypeptides. If such desirable resolution occurs, then a skewed selection of the first peak is desired. The main peak (normally 2 to 3 1.0 ml fractions, but on occasion fractions 4 to 6 1.0 ml fractions) that represent the bulk of the first peak containing the substituted polypeptide are then pooled. A typical expected yield of the SPDP-polypeptide is 50–75%.

The resulting species is a 2-pyridyl-dithio-propinate-polypeptide between the carboxyl of the propinate and an amino group in the polypeptide, wherein the N-hydroxysuccimide of the SPDP is displaced by the amino group of the polypeptide.

Next, the T cell specific binding ligand portion of b-2-M:

KDWSFYLLYYTEFTPTEKDEYAC (MW=3400)

which contains a cysteine at the carboxyl terminal is employed. To insure that this polypeptide does not form any polymeric disulfides, 6.8 mg of this polypeptide, in 1.0 ml of 0.1M sodium phosphate buffer (pH 7.0), is reduced in the presence of 10 mM dithiothretiol (hereinafter "DTT") (freshly prepared by dissolving 15.4 mg of DTT in 1.0 ml water and then adding 100 µl to the above polypeptide solution). After 45 min at room temperature, the reduced polypeptide is separated from the DTT and other products by fractionation on a P4 or P-6 column (BioRad, Richmond, Calif.). The peak fraction of the polypeptide is separately pooled.

Next, estimated equal molar portions of each polypeptide are mixed in a reaction conical stirring vessel and the reaction is allowed to proceed for 2 hours at 15° to 25° C. Under these conditions, the reduced sulfhydryl of the cysteine in the b-2-M polypeptide preferentially reacts with the 2-pyridyl-propinate-disulfide of the HIV polypeptide, the 2-pyridyl is displaced and a new disulfide is formed which results in a dipeptide bridge with a propinate residue. If desired, a chelating agent, such as 0.001 to 0.01M EDTA, may be added to reduce side reactions with contaminating heavy metals that may sometimes be introduced by, e.g., contaminated water, buffers, etc.

Then, the reaction is terminated by separation of the products and reactants on a molecular sieve and desalting column such as G-10 or G-25. In this example, a matrix, buffer and flow rate allowing separation of 1.2, 3.2 and about 5 kD materials is desired and either a P-6 or G-10 column is the preferred choice. The sample volume is approximately 5.0 ml and a column of 2.5 to 5.0 cm diameter is used. In addition, it is desirable to add stabilizers, such as 0.15M sodium chloride, 0.001M EDTA and often 0.01% (w/v) polyethylene glycol 6000 in 0.1M glycine buffer (pH 6.0), along with a bacteriostatic agent, such as 1000 units of penicillin or 10 μg/ml of streptomycin, at this stage. Further, the pH of the elution buffer can be reduced to pH 6.5 for stabilization and storage.

Alternatively, RP-HPLC separation or high voltage electrophoresis can be carried out as described above for separation and so as to determine the purity thereof. If the elution buffer used has a reduced pH, such as 5.2 or 7.0, it is desirable to use RP-HPLC.

The resulting heterofunctional cellular immunological reagent is set forth below:

KDWSFYLLYYTEFTPTEKDEYAC—SPDP—AbuTTAVPWNASWS (b-2-M 58–84) (HIV 605–620)

dimethylformamide) in a conical reaction vessel. The reaction mixture is continuously stirred for 30 min at room temperature. Then, the reaction is terminated as described below.

The products and reactants are separated by desalting on an appropriate column as described above, preferably, on a P-4 column (0.9×40 cm) at 4° C. using, as the elution buffer, 0.1M potassium phosphate buffer (pH 6.0) or 0.1M sodium phosphate buffer (pH 6.0). The pool of the relevant fractions containing the desired product is stored at 4° C. until use (normally within 24 hours). The typical yield of the MBS-polypeptide is 3.0 to 4.5 mg. The resulting polypeptide is an amino substituted polypeptide derivative of benzoic acid.

To the resulting polypeptide, estimated as 3.1 mg in 3.0 ml of 0.1M sodium phosphate buffer (pH 6.0) is added, 3.0 ml, containing 5.2 mg (2.0 μmole) of the following HIV gp41 epitope dissolved in 0.05 to 0.1M sodium phosphate buffer (pH 6.4) containing 0.15M sodium chloride and 0.01M EDTA:

RRPEGIEEEGGERDRDRSC (MW=2570)

It is important that the above buffer is deoxygenated by at least 3 repetitive cycles of vacuum-bleeding prior to use to minimize dissolved gases. Alternatively the buffer can be prepared from freshly boiled distilled or deionized water that is then stored in stoppered air-tight containers.

The reaction is allowed to continue for 3 hours at room temperature and then is terminated by the addition of 2-mercaptoethanol to a final concentration of 1.0 mM (60 μl of a 0.1M solution of 2-mercaptoethanol) followed by the addition of N-ethylmaleimide to a final concentration of 2.0 mM (60 μl of a 0.2M solution of N-ethylmaleimide).

Next, the product is purified as described above and stored at pH 6.0 to 6.5 in the presence of preservatives and other stabilizing agents, such as 10–20 mg/ml of human IgG.

The resulting heterofunctional cellular immunological reagent is set forth below:

RRPEGIEEEGGERDRDRSC—MBS—SRHRYALIPIPLAVITTAbuIVIYNleNVL (MW =0 6.0 kd)

(HIV 735–752) (LFA-3 carboxyl sequence)

SYNTHESIS EXAMPLE 3 USING MSB

The following example describes the production of a heterofunctional cellular immunological reagent comprising an HIV epitope covalently linked using MSB to the T cell specific binding ligand portion of LFA-3.

6.7 mg (2.0 μmole) of the nor-leucine, amino-butyric acid form of the T cell specific binding ligand portion of LFA-3 (see Breitmeyer, J. B., *Nature,* 329: 760 (1987) and Seed, B., *Nature,* 329: 840 (1987)):

SRHRYALIPIPLAVITTCIVIYMNVL (MW=3431)

or the derivative thereof:

SRHRYALIPIPLAVITTAbuIVIYNleNVL (MW=3385)

is dissolved in 1.0 ml of PBS. To this solution is added 50 μl of a MBS solution (4.0 μmole) (24.8 mg/ml of MBS in

SYNTHESIS EXAMPLE 4 USING CITRACONIC ANHYDRIDE AND SPDP

The following example describes the production of a heterofunctional cellular immunological reagent comprising a cat dander epitope covalently linked using SPDP to the T cell specific binding ligand portion of IL-1β, wherein the epsilon amino lysine(s) of the T cell specific ligand binding portion of IL-1β is protected in order to prevent undesirable side reactions.

The T cell specific binding portion derivative of IL-1β:

AbuggVQGEENDK (MW=1402)

is used (see Nencioni, L. et al, *J. Immunol.,* 139: 800 (1987)). However, as discussed above, it is first desirable to protect the epsilon amino lysine with, e.g., citraconic anhydride or alternatively, dimethyl maleic anhydride, to avoid undesirable side reactions.

More specifically, 2.6 mg (2.0 μmole) of the above T cell specific binding ligand of IL-1β is dissolved in 200 μl of 0.2M N-ethylmorpholine acetate and adjusted to a pH of 8.5 with 1.0N NaOH. Then, a large excess of citranoic anhydride (E. Merck, Darnstadt, West Germany or Pierce Chemical, Rockford, Ill.) (MW=112.08), calculated from the theoretical number of free amino groups (two per mole in this example, or a total of 4.0 µmole), is added in 5 to 10 equal increments (typically 5.0 µl) approximately every 5 min into a constantly stirring conical reaction vessel. The pH is monitored frequently and adjustments made with 1.0N NaOH to keep the pH at or slightly above pH 8.5. After stirring for 1 hour at room temperature, the citraconylated polypeptide is separated from the citraconic anhydride by chromatography on a P-2 column (1.5×25 cm) using 0.1N ammonium bicarbonate buffer (pH 8.5). At least 100 0.5 ml size fractions, which fractions typically represent about 1/100 of the total column volume, are collected and monitored at $A_{220}$ to $A_{280}$. The first peak containing the derivatized polypeptide is lyopholized and then stored dessicated if necessary, to obtain the polypeptide shown below:

AbuggVQGEESNDK(cit) (MW=1410)

Then, 2.8 mg of the citraconylated polypeptide (2.0 µm) is treated with SPDP as described above to obtain the polypeptide shown below:

SPDP-AbuggVQGEESNDK(cit)

Next, 8.7 mg (2.0 µmole) of a cat dander epitope:

GITPAVKRDVDLFLTGTPDEYVEQVAQYKAPDVc (MW=4333)

is coupled to the SPDP-IL-1β polypeptide described above. After coupling the IL-1β T cell specific binding ligand with the cat dander epitope as described above to form the heterofunctional cellular immunological reagent, the citraconylated groups are deblocked by removing the citranoic group by acid treatment. This is accomplished by dialysis of the 3.0 to 5.0 ml pool after the P-10 or G-10 column separation of the final product against 2 changes of 1.0 liter of 5.0% (v/v) acetic acid for 4 hours at 4° C., followed by dialysis against 2 changes of 1.0 liter of 0.05M glycine buffer (pH 6.5) containing 0.15M sodium chloride and 0.01M EDTA, for at least 2 hours and then overnight at 2° to 8° C.

The resulting heterofunctional cellular immunological reagent is shown below:

GITPAVKRDVDLFLTGTPDEYVEQVAQYKAPDVc—SPDP—AbuggVQGEESNDK (cat dander 1–33) (IL-1β 163–171)

In a second embodiment, the above-described objects of the present invention have been met by a vaccine for the prevention or treatment of disease comprising, as an active ingredient, a pharmaceutically effective amount of a heterofunctional cellular immunological reagent and a pharmaceutically acceptable carrier or diluent.

The pharmaceutically acceptable carrier employed in the present invention is not critical thereto. Examples of pharmaceutically acceptable carriers include proteins, e.g., human serum albumin and gamma-globulin or polymers, e.g., dextran or polyethylene glycol, and/or adjuvants, e.g., alum. A typical alum adjuvant is ALUGEL 50 (Serva Feinbiochemica, Heidelberg, West Germany). The amount of carrier employed is generally a 50:50 (v/w) ratio with respect to the heterofunctional cellular immunological reagent of the present invention.

The pharmaceutically acceptable diluent employed in the present invention is not critical thereto. Examples of pharmaceutically acceptable diluents include sterile 0.01 to 1.0M, preferably 0.05M glycine buffer (pH 6.5) containing 0.15M sodium chloride and 0.01M EDTA; tissue culture media such as RPMI 1640; or a physiological buffered salt solution such as Hanks Balanced Salt Solution (Life Technologies, Inc., Gaithersburg, Md.). The heterofunctional cellular immunological reagent of the present invention is generally diluted to a concentration of about 0.1 to 2000 μg/ml, preferably about 2.0 to 100 μg/ml.

In a third embodiment, the above-described objects of the present invention have been met by a method of prevention of disease comprising administering the vaccine to disease susceptible subject. A disease susceptible subject is an individual who has not previously been exposed to either the disease or has been treated for such with a vaccine and who, because of genetic, or environmental factors such as age, sex, diet, life style, lodging, etc., is at an increased risk of being exposed and/or developing the disease.

In a fourth embodiment, the above-described objects of the present invention have been met by a method of treatment of a disease comprising administering the vaccine to a subject afflicted with the disease.

The particular heterofunctional cellular immunological reagent employed as the active ingredient in the vaccine will depend upon the disease for which prevention or treatment is sought. That is, for prevention or treatment of a particular disease, one component of the heterofunctional cellular immunological reagent must be an antigen associated with the disease or a causative agent of the disease, or epitope thereof.

The amount of the heterofunctional cellular immunological reagent to be administered for prevention and/or treatment of disease will depend upon the age, weight and sex of the subject. Generally, the heterofunctional cellular immunological reagent is administered in an amount of from about 2.0 to 100 μg/70 kg of body weight, preferably about 10 to 20 μg/70 kg of body weight.

The site and mode of administration are not critical to the present invention. For example the heterofunctional cellular immunological reagent can be administered intradermally, subcutaneously, intraperitoneally, intramuscularly and, also, when an adjuvant is not employed, intravenously. A preferable mode of administration is intradermally or intramuscularly.

Multiple inoculations of the heterofunctional cellular immunological reagent are generally employed, with 3 to 4 weeks between the first and second inoculations and 6 months between the second and third inoculations. Subsequent boosters may also be employed if desired.

SYNTHESIS EXAMPLE 5

Vaccine Against Streptococcus

The following example describes the production of a vaccine for the prevention of infection by streptococcus and/or treatment of a subject infected with the same.

8.6 mg (2.0 μmole) of the streptococcal epitope:

TVTRGTISDPRVFPRGTVENPVATRSQTDTSEKC (MW=4301)

is dissolved in 2.0 ml of 0.1M potassium phosphate buffer (pH 7.5) containing 0.15M sodium chloride, reduced with 0.01M DTT for 45 min at room temperature and purified as described above.

This material is then coupled to an equal molar amount of the SPDP-derivatized b-2-M:

SPDP-AbuYVSGFHPSDIEVDLLKNGERIEKVEHSDLSFS (MW=4473)

which is formed by reacting 8.9 mg (2.0 μmole) of b-2-M with 0.05 ml of 24.8 mg/ml of SPDP (4.0 μmole) in DMSO, for 2 hours at room temperature. The resulting heterofunctional cellular immunological reagent is shown below:

TVTRGTISDPRVFPRGTVENPVATRSQTDTSKEC—SPDP—AbuYVSGFHPSDIEVDLLKNGERIEKVEHSDLSFSK (streptococcal)  (b-2-M 24–58)

After purification, the heterofunctional cellular immunological reagent is equilibrated in a 0.05M glycine buffer (pH 6.5) containing 0.15M sodium chloride, 0.01M EDTA, and 1.0 mg/ml of alum and as such, is useful as a vaccine against streptococcal infection.

In a fifth embodiment, the above-described objects of the present invention have been met by a method of diagnosing disease comprising assaying for the presence of T cells in a subject, which are active against the disease, using the heterofunctional cellular immunological reagent.

Again, the particular heterofunctional cellular immunological reagent to be used will depend upon the disease for which diagnosis is sought. That is, one component of the heterofunctional cellular immunological reagent must be an antigen associated with the disease or a causative agent of the disease, or epitope thereof for which diagnosis is sought or a control, or non-related epitope.

The particular assay employed to diagnose the disease, i.e., to determine the presence of T cells in the subject which are active against the disease, is not critical to the present invention. Examples of such assays include the lymphoproliferative assay using radioisotopes (see Cason, J. et al, *J. Immunol. Meth.*, 102: 109 (1987)); or a non-isotopic lymphoproliferative assay using 3-(4,5-dimethylthiazol-2-yl)-2,5-diphenyl tetrazolium (hereinafter "MTT") (Sigma Chemical Co., St. Louis, Mo.) (see Mosmann, T., *J. Immunol. Meth.*, 65: 55 (1983)); assays that measure cell death, such as the $Cr^{+++}$ release assay (see Chapters 9–18 in *Manual Clin. Immunol.*, Ed. Rose, N. et al (1976) and *Fund. Clin. Immunol.*, Ed. Alexander, J. W. et al (1977)); a carboxyfluorescein diacetate (hereinafter "CDTA") uptake assay (see Bruning, J. W. et al, *J. Immunol. Meth.*, 33: 33 (1980); Hansson, Y. et al, *J. Immunol. Meth.*, 100: 261 (1987); Mosmann, T., *J. Immunol. Meth.*, 65: 55 (1983); Gerlier, D. et al, *J. Immunol. Meth.*, 94: 57 (1986)); a lymphocyte migration inhibition assay (see Chapters 9–18 in *Manual Clin. Immunol.*, Ed. Rose, N. et al (1976) and *Fund. Clin. Immunol.*, Ed. Alexander, J. W. et al (1977)); a phosphorylation assay (see Samuelson, L. E. et al, *J. Immunol.*, 139: 2708 (1987)); a delayed type hypersensitivity (DHT) skin test assay (see Kadival, G. J. et al, *J. Immunol.*, 139: 2447 (1987); and Keeney, R. T. et al, *J. Immunol. Meth.*, 101: 110 (1987)); or a T cell binding assay using a dye such as 5-[(4,6-dichlorotriazin-2-yl)amino]-fluorescein hydrochloride (hereinafter "DTAF") (see Kung, P. et al, *Proc. Natl. Acad. Sci. USA*, 77: 4914 (1980)).

The lymphoproliferative assay is modified for use to test cellular immunity to a particular disease as follows. For example, samples of blood circulatory lymph node or spleenic lymphocytes, which contain T cells, are collected using the ascetic technique, by venipuncture in sterile containers, from animals immunized with an antigen associated with disease or a causative agent of disease or an epitope thereof or the heterofunctional cellular immunological reagent. Often with animals, particularly when using mice or rats and in many cases rabbits, the animals are sacrificed, for example, 14 days after an inoculation by, e.g., cervical dislocation, and the inguinal lymph nodes and/or spleen teased into a single cell suspension. If whole blood is used, as in most cases with humans, the peripheral blood or single cell lymphocytes are treated, for example, by the "Ficoll-Hypaque" method (Pharmacia, Piscataway, N.J.) and the cells resuspended and plated into sterile culture microwells. Ficoll-Hypague treatment is often carried out to remove erythrocytes, macrophages and other cells which may interfere by consuming nutrients in long term (>hours or days) assays. Their removal is desirable since this may simplify the assay and/or interpretation of the results. In many cases, especially with early and or rapid events, this separation is not necessary.

More specifically, a 96 well Costar plate is seeded at 1.0 to $5.0 \times 10^5$, preferably $2.0 \times 10^5$ cells/well in 0.2 ml of RPMI 1640 medium, supplemented with standard antibiotics, such as penicillin and streptomycin, and often 0.5 to 10% (v/v) homologous serum, e.g., normal mouse serum for murine cells or human AB serum for human cells and BSA for other types of cells.

Next, a solution that brings both 2-mercaptoethanol to a concentration of 0.00005M and the antigen associated with disease or a causative agent of disease, or an epitope thereof, to a concentration of 0.001 μg/ml to 100 μg/ml, preferably 0.01 to 10 μg/ml, or the heterofunctional cellular immunological reagent(s) at a series of concentrations, usually from about 0.0001 to 10 μg/ml, preferably 0.01 to 1.0 μg/ml, are added to the wells.

For proper design, both the use of replicates and for better control, and more meaningful results, the use of a series of related heterofunctional cellular immunological reagents, such as those shown below, are tested at several serial dilutions usually starting at 10 μg/ml.

TRVTRGTISDPRVFPRGTVENPVATRSQTDTSK—SPDP—CYVSGFHPSDIEVDLLKNGERIEKVEHSDLSFS (streptococcal)  b-2-M 24–58)

-continued

IFAGIKKANERAELIAYLKQATK—SPDP—CYVSGFHPSDIEVDLLKNGERIEKVEHSDLSFS (cytochrome C)      (b-2-M 24–58)

IFAGIKKANERAELIAYLKQATK—SPDP—VPNLRGDLQVLAQKVARTLP (cytochrome C)      (FMDV 141–160)

TRVTRGTISDPRVFPRGTVENPVATRSQTDTSK—SPDP—VPNLRGDLQVLAQKVARTLP (streptococcal)      (FMDV 141–160)

It is desirable to test the same polypeptides but employing different orientations and different methods of linking, e.g., to couple the amino group to the carboxyl polypeptide by use of a carbodiimide activated carboxyl group of an amino group.

The various microcultures are incubated from 3 to 6 days preferably 4 days at 37° C. in a 5% $CO_2$, 95% air mixture at 95% relative humidity. Then, 0.4 μCi of $^3$H-thymidine (New England Nuclear, Boston, Mass.) with a specific activity of 1.0 Ci/nmol is added to each well and incubation at 37° C. is continued for 18 hours. The incubation is terminated and the samples processed to determine the amount of incorporation of $^3$H-thymidine into DNA by use of a multiple assay sample harvester (hereinafter "MASH"). The data is analyzed for reproducibility using 4 replicates, a blank with no cells, and various specific and non-specific heterofunctional cellular immunological reagents as controls. The results are expressed as the groups's mean+/−the standard deviation of the replicates. If less than 3 of the 4 replicates are allowable, i.e., $\overline{x}$+/−S.D., the determination should be repeated. Values greater than +/−20% of the mean are excluded. To be significant, at least two different means at 2 adjacent concentrations in a series must be different by more than 50% of the controls. If the base line is significant then the data are interpreted as an inhibitory effect or a stimulatory effect. No effect means that the patient has no cellular immunity. A stimulatory effect in this assay implies helper T cell activity of a stimulatory nature and an inhibitory effect implies that the base line T cell activity is suppressed by the system.

Typical assay conditions are selected, if possible, so that without the test reagent, such as the native intact antigen or epitope thereof or a heterofunctional cellular immunological reagent of the present invention, the positive and negative control have values preferably about 2 to 3 times the background level where no cells are present. Then the positive control should give a value of at least 10, preferably 100 or more times the background level and the negative control should be the same as described above. In this case, for a sample to register as positive or significant, it should be above the first quarter percentile between the two controls.

In many cases, the first determination of the presence or absence of cellular immunity is sufficient. The clinical interpretation of the consequences is often on a case by case basis. Thus, in many cases, such as infectious disease agents, there is a desire or need to determine or develop a positive cellular immunity presence. In other conditions, such as allergies, the cellular immunity may be misdirected causing helper T cells to produce excess IgE, as opposed to IgG or other classes or subclasses of immunoglobulins. In still other cases, diagnosis may show that the correct type of T cells for cellular immunity, e.g., helper T cells for increasing antibody production may be present but what is needed is an increase in the production of cytotoxic T cells for a particular antigen associated with disease or a causative agent of disease or epitope thereof.

As discussed above, a non-isotopic lymphoproliferative assay using MTT can also be employed to test for cellular immunity to a particular disease (see Mosmann, T., *J. Immunol. Meth.*, 65: 55 (1983); and Gerlier, A. et al, *J. Immunol. Meth.*, 94: 57 (1986)).

For the use of MTT as a replacement of $^3$H-thymidine for analysis of lymphoproliferation, the cells are processed, treated and incubated as with the thymidine assay up to the point where the $^3$H-thymidine is added. Instead of adding the $^3$H-thymidine, MTT is dissolved in sterile pyrogen free PBS to a concentration of MTT of 5.0 mg/ml and freshly filtered through a 0.2 μm filter. This solution is added at a ratio of 10 μl per 100 μl of culture. The incubation is continued at 37° C. for 4 hours. Then, the incubation is terminated by centrifugation of the cells, aspiration of the fluid and resuspension and lysis of the cells. Next, the incorporated and converted MTT, in the form of a blue precipitate, is dissolved by the addition of 100 μl of acid-isopropanol solution comprising 100 μl of 0.04N HCl in isopropanol. The contents of the wells are allowed to mix by gentle mixing on an orbital shaker at room temperature and the absorbance at $A_{570}$ is read after 15 min to 1 hour.

For the use of the heterofunctional cellular immunological reagent in cytotoxicity assays as a replacement of the MHC processing and presentation for analysis of cytotoxicity, the cells are processed, treated with the heterofunctional cellular immunological reagent for the first 6–9 days as with the lympholiferative assay. At this point, a standard $Cr^{+++}$ release assay is performed. More specifically, the cells are washed and resuspended in 0.1 ml of fresh media. Then 0.1 ml of infected cells are added to effector cells at between 10 and 200% of the concentration of the effector cells. The infected cells are freshly collected the previous day from the same donor as the effector cells and infected overnight with the agent of disease from which the antigen of the heterofunctional cellular immunological reagent was derived at a multiplicity of infection of between 0.01 and 10, preferably 1.0. After an overnight infection, the cells are labelled with $CrCl_3$, in the form $^{51}$Cr, and then washed 5 to 10 times until the amount of soluble radioactivity is less than 0.01% of the cells bound. Preferably 10,000 to 1,000,000 cpm of such labelled infected target cells are added to the effector cells and then the cells incubated for 4 to 6 hours at 37° C. Next, the cells are washed 5 times with PBS, counted and the data calculated using controls.

Also, as discussed above, another assay based on CFDA uptake can be employed to test for cellular immunity to a particular disease (see Mosmann, T., *J. Immunol. Meth.*, 65: 55 (1983); and Hansson, Y. et al, *J. Immunol. Meth.*, 100: 261 (1988)).

CFDA is advantageous in that CFDA passively traverses through the cell membrane and then, as a result of intracellular enzymes, is hydrolyzed by living cells to carboxyl fluorescence which will accumulate in living cells and makes such fluorescent under blue light. More specifically, cells are prepared and treated with an antigen associated with disease or a causative agent of disease or epitope thereof, or a heterofunctional cellular immunological reagent as described above for the lymphoproliferative or MTT assay. However, instead of processing as in those assays, the cells are washed twice with sterile Hanks Balanced Salt Solution and resuspended in 25 μl thereof to which is added 5.0 μl of a freshly diluted and filtered (0.2 μm) CFDA solution. The CFDA solution is prepared as follows: 10 μl of standard stock is prepared by acetylation of 6-carboxyfluorescein, as described by Bruning, J. W. et al, *J. Immunol. Meth.*, 33: 33 (1980) (Eastman Kodak, Rochester, N.Y.) and stored as 10 mg/ml in reagent grade acetone in a dark bottle in the cold and sealed with a glass stopper. Then, 10 ml of Hanks Balanced Salt Solution buffered with 0.02M Tris-Cl (pH 7.4) or Hepes (pH 7.4) is added. After the cells are allowed to take up and hydrolyze the CFDA for a set period of time, usually 15 min incubation at 37° C., the cells are washed with fresh Hanks Balanced Salt Solution and resuspended in 0.01 to 10 mg/ml of hemoglobin to reduce background scatter and noise. The incorporated CFDA in the cells in the wells is determined by measuring the CFDA content by monitoring fluorescence with appropriate and available fluorometers that utilize this 96 wells plate configuration.

The phosphorylation assay is carried out by activation of the cells with the heterofunctional cellular immunological reagent of the present invention and the incorporation of $^{32}$P into proteins from GTP is measured. More specifically, the cells, after a short period of treatment with the heterofunctional cellular immunological reagent of the present invention, i.e., about 5 to 60 min, are incubated with, for example, 0.001 to 0.1 μCi of $^{32}$P gamma-labelled GTP for 15 to 20 min. Then, the cells are processed for determination or $^{32}$P incorporation in all of the proteins or in a specific protein, such as a specific internal protein or a specific immunoprecipitable membrane protein.

The delayed hypersensitivity type assay (DHT assay) is conducted as follows: the antigen associated with disease or a causative agent of disease or epitope thereof, or the heterofunctional cellular immunological reagent, at an appropriate concentration, usually 0.001 to 10.0 μg/ml, preferably 0.01 to 1.0 μg/ml in PBS, is introduced by use of a thin hypodermic needle and syringe, preferably 0.05 ml with a 27 gauge, into the dermal layer of skin. A region is selected where changes in shape, coloration, thickness and other properties are easily observed and measured with calipers if desired. This usually means an area with little or no hair or pigmentation. After 24 and 48 hours, the area is observed and the results are recorded, with particular note of a hematoma, induration and shape. Often for ease of comparison, standard agents known to both evoke a positive DHT reaction and to be completely inert, such as a physiologically buffered saline solution, are included at a site 1.0 to 2.0 cm removed. In the DHT assay, the test material(s) are recorded referencing their reaction to the controls (see Kadival, G. J. et al, *J. Immunol.*, 139: 2447 (1987); and Keeney, R. T. et al, *J. Immunol. Meth.*, 101: 110 (1987)).

SYNTHESIS EXAMPLE 6

Diagnostic Reagent

The following example describes the production of a T cell specific binding ligand which binds to cells which contain either MHC Class I and II molecules on the surface thereof which is useful as a diagnostic reagent.

The following polypeptide, which contains about the first 10 amino acids in proper sequence of the M protein of 3 strains of streptococcal bacteria (see Beachley, E. H. et al, *J. Exp. Med.*, 166: 647 (1987)), is treated with citraconic anhydride to block the amino group(s) of the lysine(s) as described above. After treatment with citraconic acid and subsequent purification, the molecules are reduced with 0.01M DTT to ensure that the cysteine is in an acceptable form:

TRVTRGTISVPRVFPRGTVENPVATRSQTDTSKc (MW=4209)

The above polypeptide is then coupled to an equal molar amount of the following SPDP derivative of the IL-1β polypeptide at positions 163–171:

SPDP-AbuggVQGEESNDK (MW=1401)

which is formed by reacting 2.0 mg (2.0 μm) of the IL-1β polypeptide with 0.05 ml of 24.8 mg/ml SPDP (4.0 μm) in DMSO for 2 hours at room temperature. The resulting heterofunctional cellular immunological reagent is shown below:

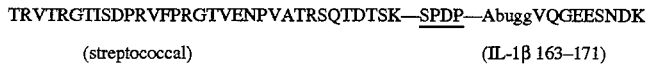

TRVTRGTISDPRVFPRGTVENPVATRSQTDTSK—SPDP—AbuggVQGEESNDK (streptococcal)　　　　　　　　　　　(IL-1β 163–171)

The following control polypeptides can be prepared in a similar manner:

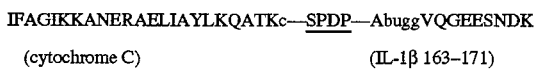

IFAGIKKANERAELIAYLKQATKc—SPDP—AbuggVQGEESNDK (cytochrome C)　　　　　　(IL-1β 163–171)

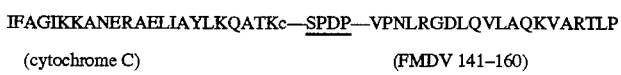

IFAGIKKANERAELIAYLKQATKc—SPDP—VPNLRGDLQVLAQKVARTLP (cytochrome C)　　　　　　(FMDV 141–160)

TRVTRGTISDPRVFPRGTVENPVATRSQTDTSK—SPDP—VPNLRGDLQVLAQKVARTLP (streptococcal)　　　　　　　　　　(FMDV 141–160)

SYNTHESIS EXAMPLE 7

Diagnostic Reagent

The following example describes the production of another T cell specific binding ligand which binds to cells which contain either MHC Class I and II molecules on the surface thereof which is useful as a diagnostic reagent.

The streptococcal derived polypeptide of Synthesis Example 6 is coupled to the derivative of concanvalin A at positions 81–110:

gggLNDVLPEWVRVGLDSASTGLYKETNTILSWS (MW=4266)

More specifically, 8.5 mg of the above concanvalin A polypeptide (2.0 μm) is reacted with 0.5 ml of the SPDP solution described in Synthesis Example 6 and then subsequently reacted with the streptococcal derived polypeptide of Synthesis Example 6 as described therein so as to obtain the following heterofunctional cellular immunological reagent:

TRVTRGTISVPRVFPRGTVENPVATRSQTDTSKc—SPDP—gggLNDVLPEWVRVGLDSASTGLYKETNTILSWS (streptococcal)          (concanvalin A)

The following control polypeptides can be prepared for the concanvalin A derivative in the same manner as described in Synthesis Example 6:

IFAGIKKANERAELIAYLKQATKc—SPDP—ggLNDVLPEWVRVGLDSASTGLYKETNTILSWS (cytochrome C)          (concanvalin A)

IFAGIKKANERAELIAYLKQATKc—SPDP—VPNLRGDLQVLAQKVARTLP (cytochrome C)          (FMDV 141–160)

TRVTRGTISDPRVFPRGTVENPVATRSQTDTSKc—SPDP—VPNLRGDLQVLAQKVARTLP (streptococcal)          (FMDV 141–160)

SYNTHESIS EXAMPLE 8

Labelled Diagnostic Reagent

The following example describes the labelling of a heterofunctional cellular immunological reagent for use in visualizing the binding of the heterofunctional cellular immunological reagent to the surface of T cells so as to diagnose the presence of T cells in a subject which are active against HIV.

5.0 mg (1.0 μmole) of the following heterofunctional cellular immunological reagent:

DWSFYLLYYTEFTPTEKDEYAC—SPDP—AbuTTAVPNASWS (b-2M 58–84)          (HIV 605–620)

obtained as described above is dissolved in 2.0 ml of 0.05M sodium phosphate buffer (pH 7.0) containing 0.15M sodium chloride and reacted with 5.0 mg (10 μmole) of DTAF (Eastman Kodak, Rochester, N.Y.) or NHS-Biotin (Pierce Chemical, Rockford, Ill.) at 15° to 25° C. so as to label the heterofunctional cellular immunological reagent. Since the heterofunctional cellular immunological reagent has a somewhat labile disulfide, the conditions are essentially as recommended by the manufacturer but the reaction is carried out for 2 hours and at a pH of 7.0 and the reaction products are immediately separated by desalting and fractionating on a G-10 column using 0.05M potassium phosphate buffer (pH 6.5) containing 0.15M sodium chloride, 0.001M EDTA, and 0.01% (w/v) PEG-6000. The resulting polypeptide is shown below:

DTAF—DWSFYLLYYTEFTPTEKDEYAC—SPDP—AbuTTAVPNASWS (b-2M 58–84)          (HIV 605–620)

The DTAF labelled heterofunctional cellular immunological reagent is used by incubating such with the T cells for 30–60 min at 2° to 8° C. Then, the T cells are washed and examined under a fluorescence microscope for the presence or absence of binding the heterofunctional cellular immunological reagent to the T cell membrane. Next, appropriate quantitation of the percentage of T cells so labelled is carried out.

If NHS-Biotin is used to label the heterofunctional cellular immunological reagent then such can be purified by use of an affinity column using avidin coupled to a solid support as described by the manufacturer, Pierce Chemical, Rockford, Ill. When NHS-biotin is used, avidin-FITC is used to visualize the binding of the heterofunctional cellular immunological reagent to T cells.

If a trifunctional immunological reagent is under analysis for diagnostic uses then a total of eight heterofunctional cellular immunological reagents are possible if two options are available for each entity. Often by grouping and taking into account combinations which are not possible to synthesize, fewer heterofunctional cellular immunological reagents are required.

SYNTHESIS EXAMPLE 9 USING SPDP AND MBS

Trifunctional Reagent

The following example describes the production of a trifunctional immunological reagent of the present invention.

6.8 mg of the following LFA-3 T cell specific binding ligand:

AbuggSRHRYALIPIPLAVITTAbuIVLYNleNV (MW=3400)

is activated with 4.0 μmole of SPDP in 0.1M potassium phosphate buffer (pH 7.5) containing 0.15M sodium chloride and subsequently purified as described above. The purified product is then reacted with 4.0 mg (2.0 μmole) of the following plasmodium CSP-1 sequence which has been freshly reduced and purified:

y(QAQGDGANAGQP)$_2$c (MW=1995)

After purification, the resulting product is reacted with 4.0 μmol of MSB to thiolyate the amino group of the tyrosine, after which the separated activated species is added to 2.0 μmole of the following b-2-M T cell specific binding ligand:

KDWSFYLLYYTEFTPTEKDEYAC (MW=3396)

to yield the trifunctional immunological reagent shown below:

KDWSFYLLYYTEFTPTEKDEYAC—MBS—y(QAQGDGANAGQP)₂c—SPDP—AbuggSRHRYALIPIPLAVITTAbuIVLYNleNGIL (b-2-M 58–84)        (CSP-1)        (LFA-3 carboxyl sequence)

While the invention has been described in detail and with reference to specific embodiments thereof, it will be apparent to one skilled in the art that various changes and modifications can be made therein without departing from the spirit and scope thereof.

We claim:

1. A heterofunctional cellular immunological product comprising at least two T cell specific binding ligands covalently linked together, wherein the T cell specific binding ligands are derived from different molecules, and wherein one of said T cell specific binding ligands is a peptide which binds to a specific class or subclass of T cells selected from the group consisting of helper T cells, suppressor T cells and cytotoxic T cells and modulates T cell activity, wherein when said T cell specific binding ligand which binds to a specific class or subclass of T cells is derived from an MHC molecule, such consists of the non-polymorphic region of the MHC molecule; and another of said T cell specific binding ligands is an antigenic peptide associated with disease or a causative agent of disease, or an epitope thereof, and wherein said product is about 20 to 100 amino acids in length.

2. The heterofunctional cellular immunological product as claimed in claim 1, wherein said T cell specific binding ligand which is a peptide which binds to a specific class or subclass of T cells is a peptide comprising a T cell binding portion of a molecule selected from the group consisting of an MHC Class I antigen, an MHC Class II antigen, lymphocyte function associated molecule-3, an antibody to CD-2, an antibody to CD-3, an antibody to CD-4, an antibody to CD-8, an antibody to lectin, a lymphokine, and a portion of the PC region of the heavy chain of immunoglobulins.

3. The heterofunctional cellular immunological product as claimed in claim 1, wherein said antigen or epitope thereof associated with disease is selected from the group consisting of an allergen, a tumor antigen, and an auto-immunity related antigen.

4. The heterofuntional cellular immunological product as claimed in claim 1, wherein the causative agent of disease to which the antigen or epitope thereof is associated is selected from the group consisting of prions, viruses, bacteria, fungi, protozoa and parasites.

5. The heterofunctional cellular immunological product as claimed in claim 1, wherein said product is about 40 to 60 amino acids in length.

* * * * *